(12) United States Patent
Pace-Asciak

(10) Patent No.: US 6,673,785 B1
(45) Date of Patent: Jan. 6, 2004

(54) USE OF HEPOXILINS OR HEPOXILIN ANALOGS AS ANTIDIABETICS, ANTIINFLAMMATORY AGENTS

(76) Inventor: Cecil R. Pace-Asciak, 218 Rose Park Dr., Apt. 2, Toronto, Ontario (CA), M4T 1R5

( * ) Notice: Subject to any disclaimer, the term of this patent is extended or adjusted under 35 U.S.C. 154(b) by 0 days.

(21) Appl. No.: 10/048,863

(22) PCT Filed: Aug. 3, 2000

(86) PCT No.: PCT/CA00/00896

§ 371 (c)(1),
(2), (4) Date: Feb. 4, 2002

(87) PCT Pub. No.: WO01/10422

PCT Pub. Date: Feb. 15, 2001

Related U.S. Application Data

(60) Provisional application No. 60/147,143, filed on Aug. 4, 1999, and provisional application No. 60/208,304, filed on Jun. 1, 2000.

(51) Int. Cl.$^7$ ............................................. A61K 31/33
(52) U.S. Cl. ........................................ 514/183; 514/866
(58) Field of Search ................................. 514/183, 866

(56) References Cited

U.S. PATENT DOCUMENTS 5,616,607 A    4/1997   Pace-Asciak et al.

FOREIGN PATENT DOCUMENTS

EP    WO 94 22848    10/1994

OTHER PUBLICATIONS

Pace–Asciak et al., "Hepoxillins raise circulating insulin levels in vivo", FEBS Letters (1999), 461(3), pp. 165–168.*
Pace–Asciak et al., Isolation and Structure of Two Hydroxy Epoxide Intermediates in the Formation of 8,11,12– and 10,11,12–Trihydroxyeicosatrienoic Acids, (1983), J. Biol. Chem., v. 258, pp. 6835–6840.
Pace–Asciak et al., Resolution by DEAE–Cellulose Chromatography of the Enzymatic Steps in the Transformation of Arachidonic Acid into 8,11,12–and 10,11,12–Trihydroxy–Eicosatrienoic Acid by the Rat Lung, (1983) Prostaglandins, v. 25, pp. 79–84.
Pace–Asciak et al., Oxygenation of Arachidonic Acid into 8,11,12– and 10,11,12–Trihydroxyeicosatrienoic Acid by Rat Lung, (1983) Advances in Prostaglandin, Thromboxane, and Leukotriene Research, v. 11, pp. 133–134.
Pace–Asciak, C., Demonstration Through [$^{18}$O] Oxygen Studies of an Intramolecular Transfer of the Terminal Hydroxyl Group of (12S)–Hydroperoxyeicosa–5,8,10, 14–Tetraenoic Acid to Form Hydroxyepoxides, (1984), J. Biol. Chem., v. 259, pp. 8332–8337.
Pace–Asciak et al., Hemoglobin– and Hemin–Catalyzed Transformation of 12$_L$–Hydroperoxy–5,8,10,14–Eicosatetraenoic Acid, (1984), Biochimica et Biophysica Acta, v. 793, pp. 485–488.
Pace–Asciak et al., Hepoxilin, A New Family of Insulin Secretagogues Formed by Intact Rat Pancreatic Islets[1], (1984), Prostaglandins Leukotrienes and Medicine, v. 16, pp. 173–180.
Pace–Asciak, C., Hepoxilins, Potential Endogenous Mediators of Insulin Release, (1986), Prog. Lipid Res., v. 25, pp. 625–628.
Anton R. et al., Occurrence of Hepoxilins and Trioxilins in Psoriatic Lesions, (1998), J. Investigative Dermatology, Inc., v. 110, pp. 303–310.
Maghaddam et al., Discovery of the Mammalian Insulin Release Modulator, Hepoxilin $B_3$, from the Tropical Red Algae *Platysiphonia miniata* and *Cottoniela filamentosa*, (1990), J. Biol. Chem. v. 265, pp. 6126–6130.
Laneuville et al., Hepoxilin $A_3$ Increases Vascular Permeability in the Rat Skin, (1991), Eicosanoids, v. 4, pp. 95–97.
Demin, Peter, M., Synthesis of Racemic 11,12–Cyclopropyl analogs of Hepoxilins $A_3$ and $B_3$, (1993), Tetrahedron Letters, v. 34, pp. 4305–4308.
Pace–Asciak, C., Hepoxilins, (1993), General Pharmacology, v. 24, pp. 805–810.
Wang et al., Stereoselective actions of Hepoxioins A3 and B3 and their Cyclopropane Analogs (HX $A_3$ and HX $B_3$) on Bradykinin and PAF–Evoked Potentiation of Vascular Leakage in Rat Skin (1999) General Pharmacology, v. 33, pp. 377–382.

\* cited by examiner

*Primary Examiner*—Kevin E. Weddington
(74) *Attorney, Agent, or Firm*—Dinsmore & Shohl LLP

(57) ABSTRACT

The present invention relates to the use of native hepoxilins and of hepoxilin analogs for the regulation of insulin secretion and to the use of hepoxilin analogs as anti-inflammatory, anti-diabetic and anti-thrombotic compounds.

14 Claims, 28 Drawing Sheets

2D-gels showing specific binding protein (see arrow) labeled with photo ligand (preliminary data)

2D-gels showing specific binding protein (see arrow) labeled with photo ligand (preliminary data)

US 6,673,785 B1

USE OF HEPOXILINS OR HEPOXILIN ANALOGS AS ANTIDIABETICS, ANTIINFLAMMATORY AGENTS

The present application is a 371 of PCT/CA00/00896 filed Aug. 3, 2000 and claims priority under 35 U.S.C. §119 of U.S. applications Ser. Nos. 60/147,143 filed Aug. 4, 1999 and 60/208,304 filed Jun. 1, 2000.

FIELD OF THE INVENTION

The present invention relates to therapeutic methods and pharmaceutical compositions employing native hepoxilins and hepoxilin analogs.

BACKGROUND OF THE INVENTION

Hepoxilins are biologically active hydroxy epoxide derivatives of arachidonic acid formed through the 12-lipoxygenase pathway (Pace-Asciak et al. (1983), *J. Biol. Chem.*, v. 258, pp. 6835–6840; Pace-Asciak et al. (1983), *Prostaglandins*, v. 25, pp. 79–84; Pace-Asciak et al. (1984), *Biochem. Biophys. Acta*, v. 793, pp. 485–488). They are formed from 12-HPETE, an unstable hydroperoxide derivative of arachidonic acid (Pace-Asciak et al. (1983), *Adv. Prostagl. Throm. Leuk. Res.*, v. 11, pp. 133–134; Pace-Asciak (1984), *J. Biol. Chem.*, v. 259, pp. 8332–8337). Four natural hepoxilins have been isolated and identified, hepoxilin $A_3$ [8(S,R)-hydroxy-11(S),12(S)-epoxy-eicosa-5Z, 9E, 14Z-trienoic acid] and hepoxilin $B_3$ [10(S,R)hydroxy-11(S), 12(S)-epoxy-eicosa-5Z, 8Z, 14Z-trienoic acid].

These products of an arachidonic acid pathway have been implicated in the mediation of inflammation and smooth muscle contraction by modulation of second messenger calcium response pathways. Hepoxilins have been demonstrated to raise intracellular calcium in human neutrophils in vitro. Hepoxilins have also been demonstrated to be involved in the in vitro release of insulin by pancreatic islet cells (Pace-Asciak et al. (1986), *Progr. Lipid Res.*, v. 25, pp. 625–628), although nothing has been published on the action of hepoxilin analogs on such cells.

U.S. Pat. No. 5,616,607 discloses hepoxilin analogs found to antagonize hepoxilin activity and stated to be useful in the modulation of hepoxilin-mediated processes such as inflammation and in the modulation of other processes mediated by cellular calcium levels. It is suggested that hepoxilin analogs may have utility in diabetes. However, the in vivo activity of hepoxilin analogs has never been demonstrated nor has an increased in vivo efficacy of any hepoxilin analogs been demonstrated with respect to either insulin secretion or the inflammatory process.

SUMMARY OF THE INVENTION

In accordance with the present invention, there are provided hepoxilin analogs for use in the regulation of insulin secretion, for the treatment and prevention of both acute and chronic inflammation in a mammal and for decreasing/preventing lung fibrosis in vivo. For the first time it has been demonstrated that certain hepoxilin analogs have a good efficacy or increased potency in mammals in vivo. Native hepoxilin has been referred to herein generally as "HX".

In accordance with one embodiment of the present invention is a method for regulating insulin secretion in a mammal comprising administering an effective amount of a native hepoxilin or hepoxilin analog to said mammal.

According to a further embodiment of the present invention is a method for changing the plasma insulin levels in a mammal, the method comprising administering an effective amount of a native hepoxilin or hepoxilin analog to said mammal.

According to yet another embodiment of the invention is a method for altering plasma glucose levels in a mammal, the method comprising administering an effective amount of a native hepoxilin or hepoxilin analog to said mammal.

The hepoxilin analogs of the present invention also have use in various types of binding assays to identify hepoxilin binding proteins and to identify other forms of such binding proteins as exist for example in diabetes and as such provide a means for diagnosing diabetes in the prediabetic stage. The hepoxilin analogs may also be used in various in vitro assays to study second messenger downstream effects after receptor binding.

In accordance with the present invention are hepoxilin analog photoligands for use in binding studies, most preferably for use in binding studies identifying the hepoxilin binding protein. It is understood by one skilled in the art, that the hepoxilin analogs of the present invention can be chemically modified, for example radioactively labelled as required, for various uses in different assay systems.

The hepoxilin binding proteins have been demonstrated to be G protein coupled as the binding of hepoxilin as well as calcium release is inhibited by non-hydrolyzable analogs of GTP. Additionally, hepoxilin binding causes a rise in cyclic AMP formation indicating that binding is coupled to a Gs-protein. Thus, in accordance with a further embodiment of the invention, is the use of hepoxilin analogs to increase cAMP formation. Hepoxilin and its analogs can be used to elicit second messenger systems via binding to the hepoxilin binding protein.

According to a further embodiment of the invention is a method for treating an inflammatory disorder in a animal comprising administering to the mammal in need of such treatment a therapeutically effective amount of a hepoxilin analog.

According to another embodiment of the invention is a composition for treating an inflammatory disorder in a mammal, the composition comprising a therapeutically effective amount of a hepoxilin analog and a pharmaceutically acceptable carrier.

According to a further embodiment of the invention is a method for treating in a mammal a disorder which involves the development of lung fibrosis, the method comprising administering to the mammal in need of such treatment a therapeutically effective amount of a hepoxilin analog.

According to another embodiment of the invention is a composition for treating a disorder in a mammal which involves the development of lung fibrosis, the composition comprising a therapeutically effective amount of a hepoxilin analog and a pharmaceutically acceptable carrier.

According to a further embodiment of the invention is a method for treating conditions where an anti-coagulative effect is desired, in a mammal, the method comprising administering to the mammal in need of such treatment a therapeutically effective amount of native hepoxilin or a hepoxilin analog.

According to another embodiment of the present invention is a method for modulating vascular tone in a mammal, the method comprising administering to the mammal in need of such treatment a therapeutically effective amount of native hepoxilin or a hepoxilin analog.

According to another embodiment of the present invention is a method for decreasing vascular permeability in a mammal, the method comprising administering to the mammal in need of such treatment a therapeutically effective amount of native hepoxilin or a hepoxilin analog.

According to a further embodiment of the present invention is the use of a native hepoxilin or a hepoxilin analog for decreasing the vascular side effects of chemotherapeutic agents.

According to another embodiment of the invention is a method for reducing or preventing side effects of treatment for malignancy in a mammal wherein the mammal is concurrently receiving a chemotherapeutic agent, the method comprising administering to the mammal in need of such treatment a therapeutically effective amount of a hepoxilin analog and a pharmaceutically acceptable carrier.

According to yet a further embodiment of the present invention is the use of a native hepoxilin or hepoxilin analog for decreasing collagen synthesis associated with tissue fibrosis.

BRIEF DESCRIPTION OF THE DRAWINGS

Certain embodiments of the invention are described with reference to the following drawings, wherein

FIG. 13A, saline control (no bleomycin); FIG. 13B (bleomycin+saline); FIG. 13C (bleomycin+Trolox antioxidant in saline); FIG. 13D (bleomycin+H1 in saline); FIG. 13E (bleomycin+H2 in saline); FIG. 13F (bleomycin+H3 in saline); FIG. 13G (bleomycin+H4 in saline). All compounds (except bleomycin which was injected at the start only) were injected i.p. daily for 8 days. At the end of the study, lungs were inflated, perfused and fixed for H&E staining.

FIGS. 14A through 14E shows the protective actions of various concentrations of analog H1 in a bleomycin-induced lung injury mouse model: Panel A, saline control (no bleomycin); Panel B (bleomycin+saline), Panel C (bleomycin+400 µg/kg H1 in saline); Panel D (bleomycin+2 mg/kg H1 in saline); and, Panel E (bleomycin+4 mg/kg H1 in saline) (HXA-1 to 4=H1 to 4).

FIGS. 19A and 19B show the effect of H1 (HXA-1) and H2 on skin vascular permeability. Areas are also shown where bleomycin or saline were used as controls.

Figure 1:
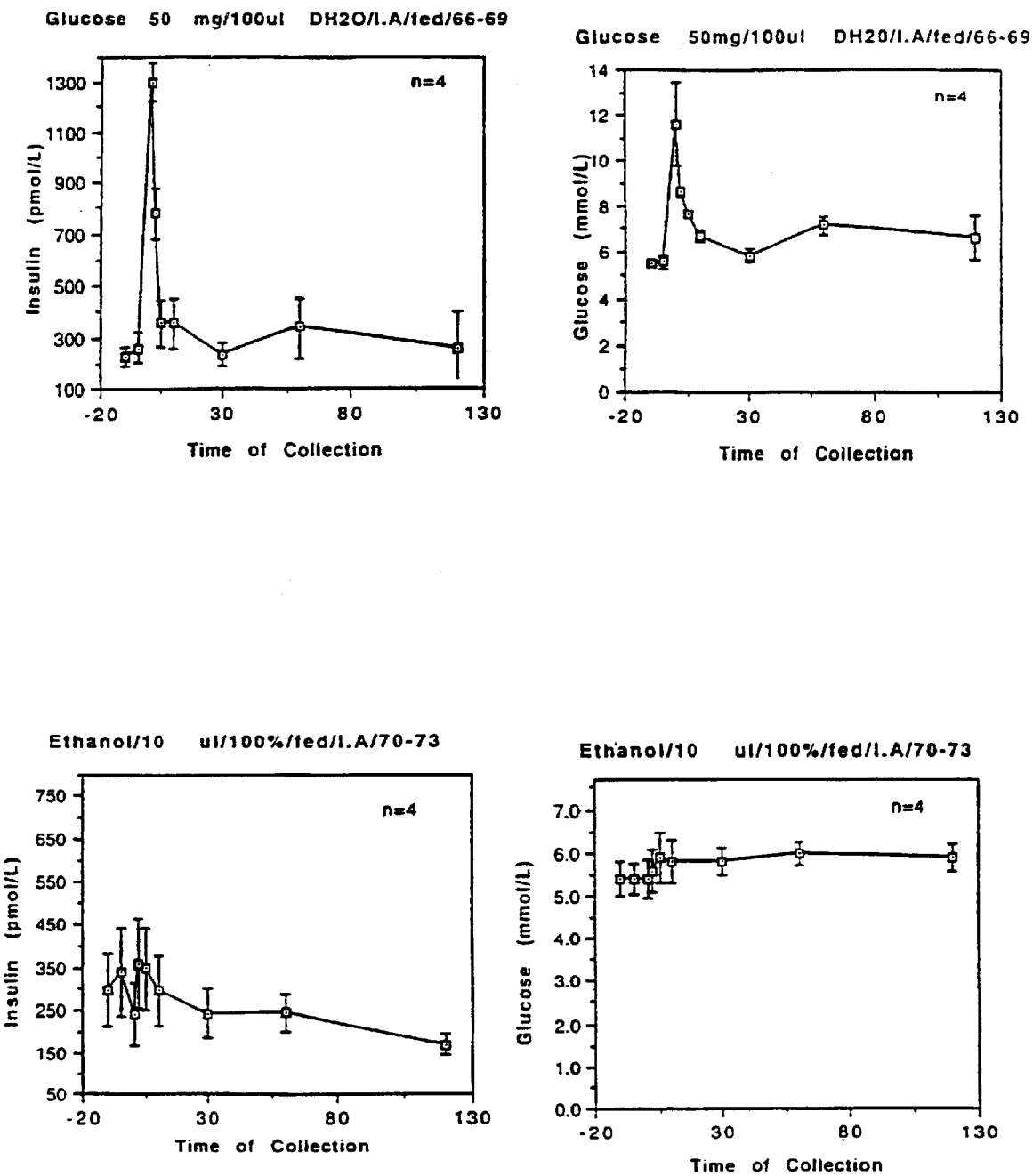
FIG. 1 shows changes in plasma insulin and plasma glucose concentrations after bolus i.a. administration of glucose (50 mg/100 µl) or ethanol (10 µl), the vehicle for hepoxilin (HX) analogs, in the fed rat. The injection of the test compounds was carried out in a Y-cannula attached to the carotid artery through which the test compound in 10 µl ethanol was injected while 300 µl saline was being injected. Hence the test compound was 'carried' into the circulation by the saline. The total time of injection was 5 sec.

In the drawings, preferred embodiments of the invention are illustrated by way of example. It is to be understood that the description and drawings are only for the purpose of illustration and as an aid to understanding and are not intended as a definition of the limits of the invention.

DETAILED DESCRIPTION OF THE INVENTION

The present invention provides methods and pharmaceutical compositions for treating a number of disorders. These methods and compositions employ native hepoxilins or hepoxilin analogs.

Four natural hepoxilins are known, two epimers of hepoxilin $A_3$ (8S and 8R) and two epimers of hepoxilin $B_3$ (10S and 10R); these hepoxilins are referred to herein as $HxA_3$ (8S), $HxA_3$ (8R), $HxB_3$ (10S) and $HxB_3$ (10R) respectively.

In the hepoxilin analogs of the invention, the epoxide at C11–C12 of the native hepoxilins is replaced by another group, such as S, —NH or —$C_nH_{n+2}$ where n is 1 to 4. Hepoxilin analogs which may be used in the methods of the invention comprise compounds of the formula

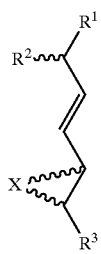

(I)

wherein X=O, $CH_2$, S or NH;

$R^1$=lower alkyl or alkene;
  lower alcohol (C1 to C22), saturated or unsaturated; or
  —$CH_2CH$=CH—$(CH_2)_3$—COR" wherein R"=OH or O—lower alkyl or alkene;

$R^2$=OH, $NH_2$, SH, $OPO_3H$, lower alkyl or alkene or O—lower alkyl or alkene; and $R^3$ =lower alkyl or alkene or
  —$CH_2$—CH=CH—$(CH_2)_3$—R'" wherein R'"=$CH_3$, $CH_2OH$ or $CH_2$
  —O—lower alkyl or alkene

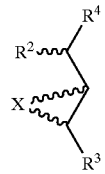

(II)

wherein X, $R^1$, $R^2$ and $R^3$ are as in formula I and $R^4$=lower alkyl or alkene; lower alcohol (C1 to C22), saturated or unsaturated; or
  —CH=CH—$CH_2$—CH=CH—$(CH_2)_3$—COR"
wherein R'=OH or O—lower alkyl or alkene.

Preferred hepoxilin analogs are:

delta $HxA_3$-LP=8(S)-hydroxy-11,12-cyclopropyl-eicosa-5Z, 10E, 14Z-trienoic acid methyl ester or free acid;

delta $HxA_3$-MP=8(R)hydroxy-11,12-cyclopropyl-eicosa-5Z, 10E, 14Z-trienoic acid methyl ester or free acid;

delta $HxB_3$-LP=10(S)-hydroxy-11,12-cyclopropyl-eicosa-5Z, 8Z, 14Z-trienoic acid methyl ester or free acid; and delta $HxB_3$-MP=10(R)-hydroxy-11, 12-cyclopropyl-eicosa-5Z, 8Z, 14Z-trienoic acid methyl ester or free acid; the methyl esters are designated herein as H1, H2, H3 and H4 respectively. These analogs are described in U.S. Pat. No. 5,616,607, the contents of which are incorporated herein by reference.

As used herein, "alkyl" means a branched or unbranched alkyl radical. "Lower alkyl or alkene" means C1 to C22 alkyl or alkene.

Native hepoxilins and the hepoxilin analogs described herein have been shown to stimulate insulin release and to increase blood insulin levels in vivo in mammals. These compounds therefore provide a new method and new pharmaceutical compositions for regulating insulin secretion and glycemia in diabetes especially in Type II diabetes.

The hepoxilin analogs described herein have also been shown to delay the onset of diabetes in NOD mice injected with cyclophosphamide and provide a means of delaying or preventing the development of diabetes in susceptible subjects.

A specific hepoxilin-binding protein has also been demonstrated in normal human neutrophils and has been resolved on 2D-PAGE to show one main protein band using an HX photoaffinity radioligand. In contrast, the hepoxilin-binding protein from Type 1 and Type II diabetic subjects was resolved into at least three isoforms on 2D-PAGE. The present study demonstrates that intact human neutrophils from diabetic subjects are more responsive to a dose regimen of native HX than those from normal subjects in terms of calcium release in vitro. It appears that the hepoxilin analogs herein disclosed can be used in various assay systems to identify and characterize the hepoxilin receptor in both normal and diabetic patients.

A diagnostic test for pre-diabetes may therefore by carried out by examining the neutrophil HX-binding protein by 2D-PAGE, with detection using an HX photo affinity radioligand, as described in the examples herein. Suitable derivatives for such radioligands include compounds of formula I or II wherein $R^3$=$CH_2$—CH=CH—$(CH_2)_3$-R'" wherein R'"=$CH_2$—OCO-phenyl or $CH_2$—OCO-phenyl substituted with $N_3$ and $SnBu_3$ and its corresponding iodine derivative.

The lung reacts to a number of insults by undergoing fibrosis, which impairs lung function and leads to morbidity and eventually, in severe cases, death. Lung fibrosis can occur, for example, as a result of bacterial infections or shock or as a result of hyperoxygenation when patients breathe pure oxygen or oxygen-enriched air. Lung fibrosis is also a frequent and serious side-effect of cancer chemotherapy, for example, with the drug bleomycin.

Bleomycin-induced lung injury provides an accepted animal model for lung fibrosis. It has been shown that treatment with the hepoxilin analogs described herein provided protection against lung fibrosis in this model, with reduced pulmonary fibrosis and edema, reduced collagen synthesis, reduced vascular permeability and reduced inflammatory response.

In accordance with the methods and compositions of the present invention, one or more hepoxilin analogs may be administered to a mammal in a variety of forms depending on the selected route of administration, as will be understood by those skilled in the art. The compositions of the invention may be administered orally or parentally, the latter route including intravenous and subcutaneous administration. Parenteral administration may be by continuous infusion over a selected period of time. Forms for injectable use include sterile aqueous solutions or dispersion and sterile powders for the extemporaneous preparation of sterile injectable solutions or dispersions. In all cases the form must be sterile and must be fluid to the extent that easy syringability exists.

The hepoxilin analog may be orally administered with an inert diluent or with an assimilable edible carrier, or it may be enclosed in hard or soft shell gelatin capsules, compressed into tablets or incorporated directly with the food of the diet. For oral therapeutic administration, a hepoxilin analog may be incorporated with excipient and used in the form in ingestible tablets, buccal tablets, troches, capsules, elixirs, suspensions, syrups, wafers and the like.

Compositions containing one or more hepoxilin analogs of the present invention can also be administered in a solution or emulsion contained within phospholipid vesicles called liposomes. The liposomes may be unilamellar or multilamellar and are formed of constituents selected from phosphatidylcholine, dipalnmitoylphosphatidylcholine, cholesterol, phosphatidylethanolamtine, phosphatidylserine. dimyristoylphosphatidylcholine and combinations thereof. The multilamellar liposomes comprise multilamellar vesicles of similar composition to unilamellar vesicles, but are prepared so as to result in a plurality of compartments in which the analogs containing solution or emulsion is entrapped. Additionally, other adjuvants and modifiers may be included in the liposomal formulation such as polyethyleneglycol, or other materials.

The liposomes containing the hepoxilin analog compositions may also have modifications such as having antibodies immobilized on the surface of the liposome in order to target their delivery.

In one embodiment of the present invention is a pharmaceutical composition for administration to subjects in a biologically compatible form suitable for administration in vivo for treating an inflammatory disorder, lung fibrosis or diabetes and comprising a safe and effective amount of a hepoxilin analog alone, or in combination with other agents and pharmaceutical carriers. The composition may be administered to any living organism in need of such treatment including humans and animals as the composition has efficacy in vivo. By safe and effective, as used herein, is meant providing sufficient potency in order to decrease, prevent, ameliorate or treat the disease affecting the subject while avoiding serious side effects. A safe and effective amount will vary depending on the age of the subject, the physical condition of the subject being treated, the severity of the disorder, the duration of treatment and the nature of any concurrent therapy, and its determination is within the skill of the ordinary physician.

A therapeutically active amount of a pharmaceutical composition of the present invention means an amount effective, at dosages and for periods of time necessary to achieve the desired result. This may also vary according to factors such as the disease state, age, sex, and weight of the subject and the ability of the hepoxilin analog to elicit a desired response in the subject. Dosage regima may be adjusted to provide the optimum therapeutic response. For example, several divided doses may be administered daily or the dose may be proportionally reduced as indicated by the exigencies of the therapeutic situation.

By pharmaceutically acceptable carrier as used herein is meant one or more compatible solid or liquid delivery systems. Some examples include but are not limited to starches, sugars, cellulose and its derivatives, powdered tragacanth, malt, gelatin, collagen, talc, stearic acids, magnesium stearate, calcium sulfate, vegetable oils, polyols, agar, alginic acids, pyrogen free water, isotonic saline, phosphate buffer, and other suitable non-toxic substances used in pharmaceutical formulations. Other excipients such as wetting agents and lubricants, tableting agents, stabilizers, anti-oxidants and preservatives are also contemplated.

The compositions described herein can be prepared by known methods for the preparation of pharmaceutically acceptable compositions which can be administered to subjects, such that an effective quantity of the hepoxilin analog or analogs is combined in a mixture with a pharmaceutically acceptable carrier. Suitable carriers are described for example in Remington's Pharmaceutical Sciences (Mack Publishing Company, Easton, Pa., USA, 1985). On this basis the compositions include, albeit not exclusively, solutions of the hepoxilin analog(s) in association with one or more pharmaceutically acceptable vehicles or diluents, and contained in buffered solutions with a suitable pH and iso-osmotic with the physiological fluids. Hepoxilin analogs may be prepared as described, for example, in U.S. Pat. No. 5,616,607.

As hepoxilin binding to the hepoxilin binding protein has been demonstrated to be coupled to a G-protein which promotes cAMP formation, hepoxilin analogs may have use in the general activation of G proteins and increasing cAMP levels. This may have a general significance where such activation is shown to have a desired physiological effect such as in platelet aggregation. Thus native hepoxilin and hepoxilin analogs may have clinical relevance with respect to anti-coagulation and therefore in various disease states associated with the cardiovascular system for example where it would be beneficial to prevent/treat blood clots in vessels. Both native hepoxilin and hepoxilin analog action on second messenger systems may also be significant with respect to use for modulating vascular tone.

In accordance with the present invention, native hepoxilin and hepoxilin analogs also have clinical relevance with respect to therapeutic treatment in cancer and treatment-associated lung disease, preventing the serious vascular side effects of chemotherapeutic agents such as bleomycin for example.

EXAMPLES

The examples are described for the purposes of illustration and are not intended to limit in any way the scope of the invention.

Methods of biochemistry and protein chemistry referred to but not explicitly described in this disclosure and examples are reported in the scientific literature and are well known to those skilled in the art.

Example 1

Hepoxilin Analogs Cause a Rise in Plasma Insulin in the Inactin-anaesthetised Rat After i.a. Administration in the Fed but not the Fasted Rat Rats were divided into groups of 5, and after Inactin anaesthesia, tracheotomy was performed. The animals were heparinized. The carotid artery was cannulated for sample injection (glucose at 50 mg/100 $\mu$l saline and test compounds (100 $\mu$g) as a bolus in 10 $\mu$l ethanol injected during flushing of the cannula with 300 $\mu$l saline) and blood sampling. Each animal was subjected to blood sampling at the following time points, i.e. −10 and −5 minutes, 30 sec after injection of test compound and 2, 5, 10, 30 and 60 min. Blood samples at the end of the experiment were centrifuged and the serum was transferred to plastic tubes and analyzed for both insulin and glucose. Insulin was measured by RIA.

The following compounds were tested: hepoxilin analogs: H1, H2, H3, H4; natural hepoxilins: $HxA_3$-8S, $HxA_3$-8R, $HxB_3$-10S, $HxB_3$-10R.

Glucose was tested at a concentration of 50 mg/100 $\mu$l injection which yields a blood level of approx. 13 mM, and ethanol vehicle (10 $\mu$l) was also tested in a set of animals. All hepoxilins were tested at 100 $\mu$g/200 g rat body in weight in 10 $\mu$l ethanol and added through a Y injector into a 300 $\mu$l stream of heparinized saline. The sample injection took 5 sec.

Figure 2:
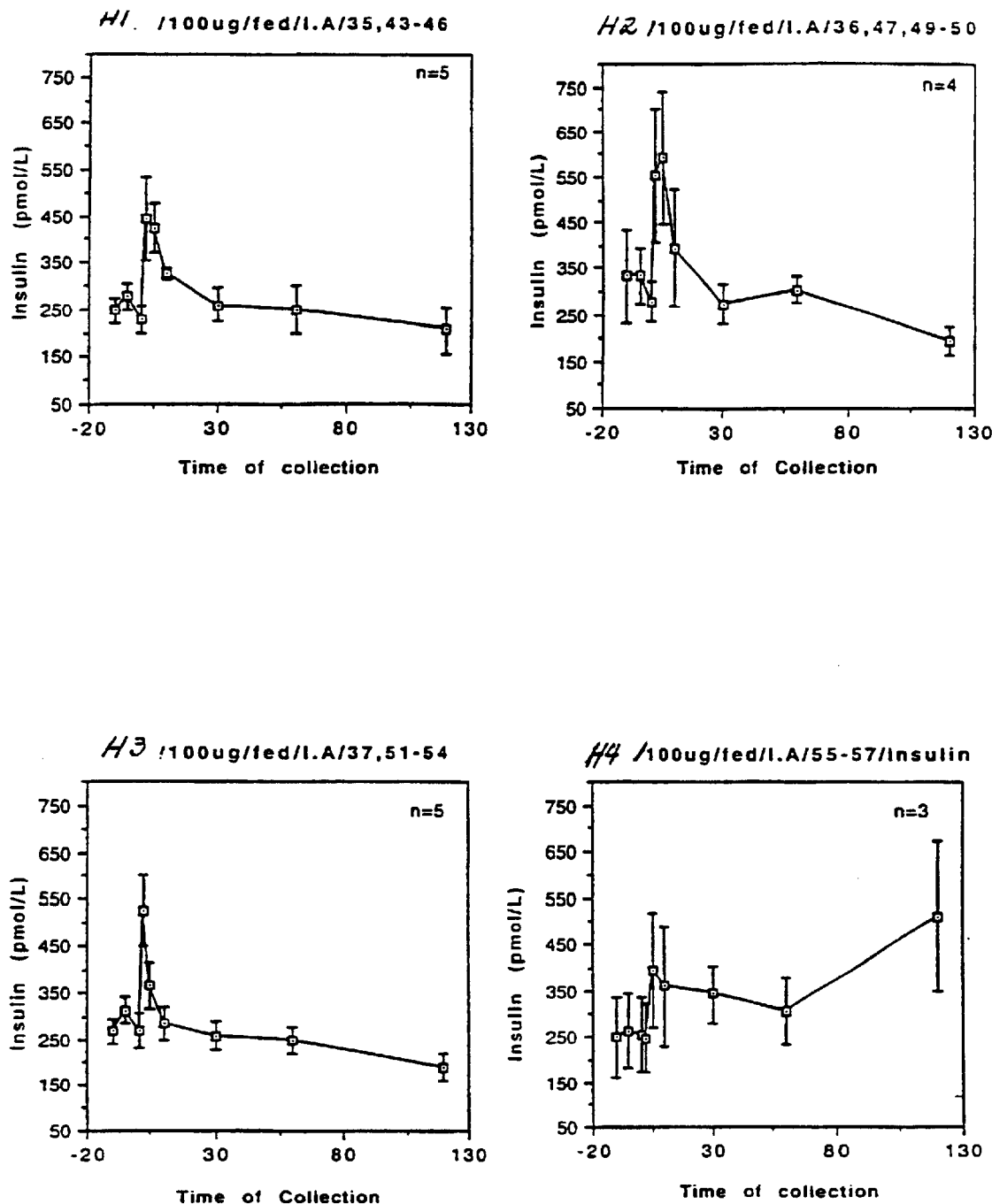
FIG. 2 shows changes in plasma insulin concentration produced by each of the four HX analogs, H1–H4, at 100 µg/10 µl ethanol (i.a. details as in FIG. 1).
Figure 3:
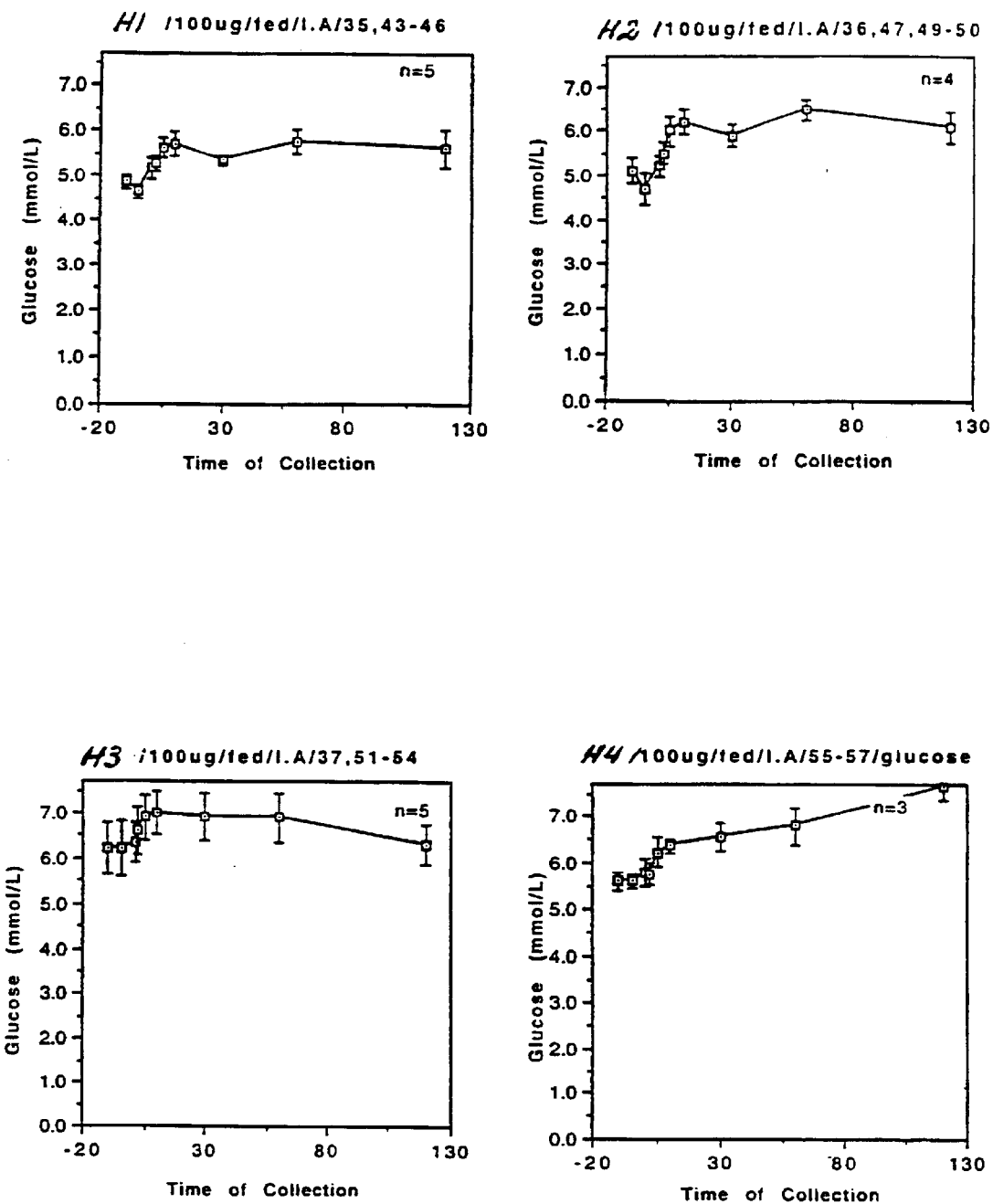
FIG. 3 shows changes in plasma glucose concentrations after i.a. administration of each of the four HX analogs as in FIG. 2.
Figure 4:
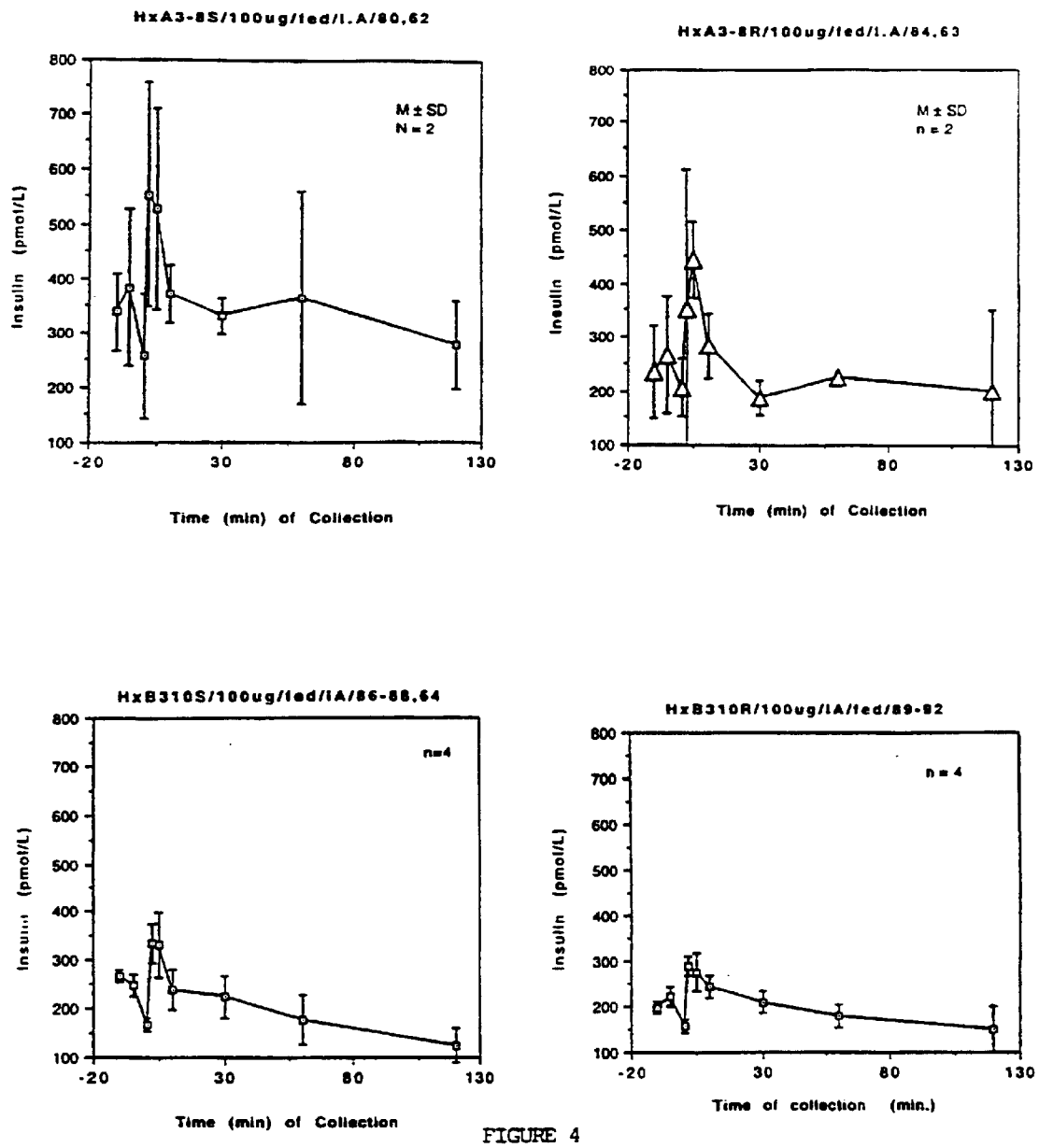
FIG. 4 shows changes in plasma insulin concentration produced by each of the four native HXs, at 100 µg/10 µl ethanol (i.a. details as in FIG. 1).
Figure 5:
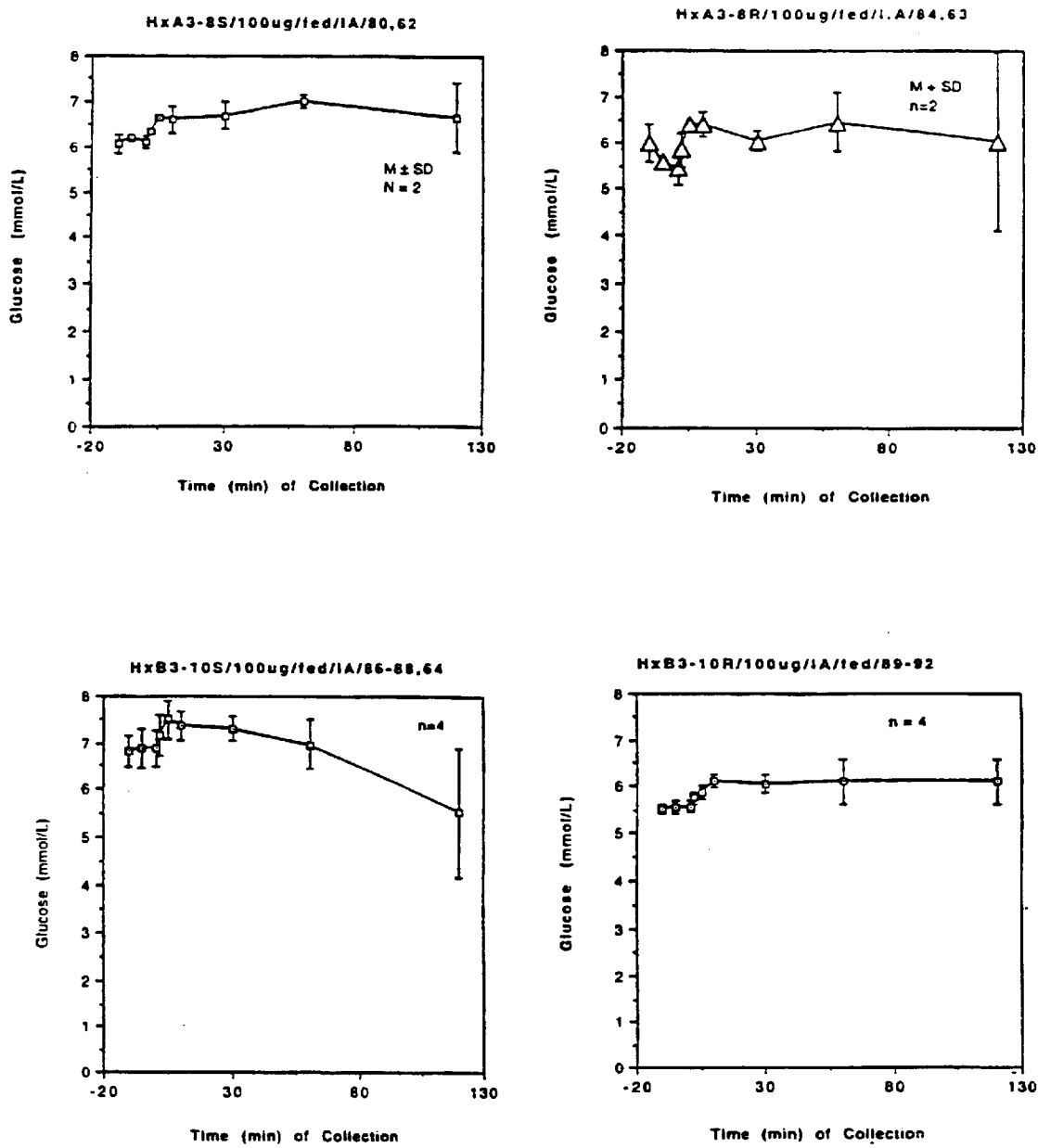
FIG. 5 shows changes in plasma glucose concentrations after i.a. administration of each of the four native HXs as in FIG. 4.

The experiments were performed in fasted rats and rats that were allowed free access to food and water. While the former did not yield interesting or significant data (with the exception of the glucose group), animals that were allowed free access to food gave highly significant data showing release of insulin in the circulation. Results are summarized in FIGS. 1 to 5. A good response to glucose administration was observed for both plasma insulin and glucose, while the ethanol vehicle (for the test compounds) gave no significant changes in plasma insulin (FIG. 1). Results comparing the effects of the four HX analogs (H1–H4) are seen in FIG. 2 for plasma insulin levels. It is clear that all 4 analogs cause highly significant changes in the release of insulin peaking at about 2 min after ia. injection (circulation time in the rat is approx. 6 sec., i.e. the peak effect is approx after 20 circulations) but the compounds differ in potency. Minimal changes in plasma glucose concentrations resulting after addition of each compound were seen (FIG. 3). FIGS. 4 and 5 compare the effect of the 4 native hepoxilins (A3 (8S and 8R) and $B_3$ (10S and 10R)) on plasma insulin and glucose respectively at the same doses. All scales were maintained the same for easy comparison with the exception of the experiments where glucose was administered. Again changes in plasma insulin levels but not in glucose levels, were seen with the four native hepoxilins.

Example 2

A Specific Hepoxilin-binding Protein in Human Neutrophils Exists Which has Been Resolved on 2D-PAGE Into One Main Protein Band Using an HX Photoaffinity Radioligand.

Figure 6:
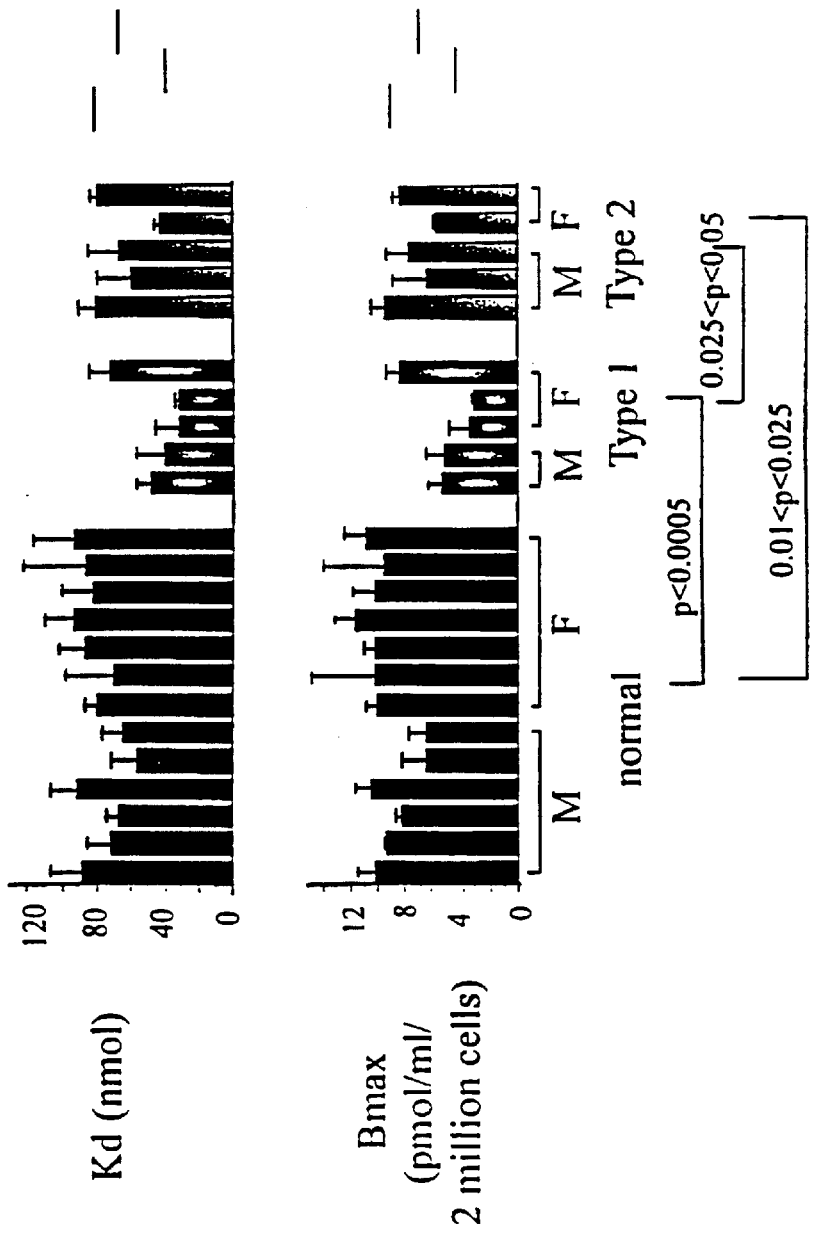
FIG. 6 shows a comparison of Kd and Bmax for the binding of tritiated HX to neutrophil membranes from human normals, Type 1 and Type 2 diabetic subjects.
Figure 7:
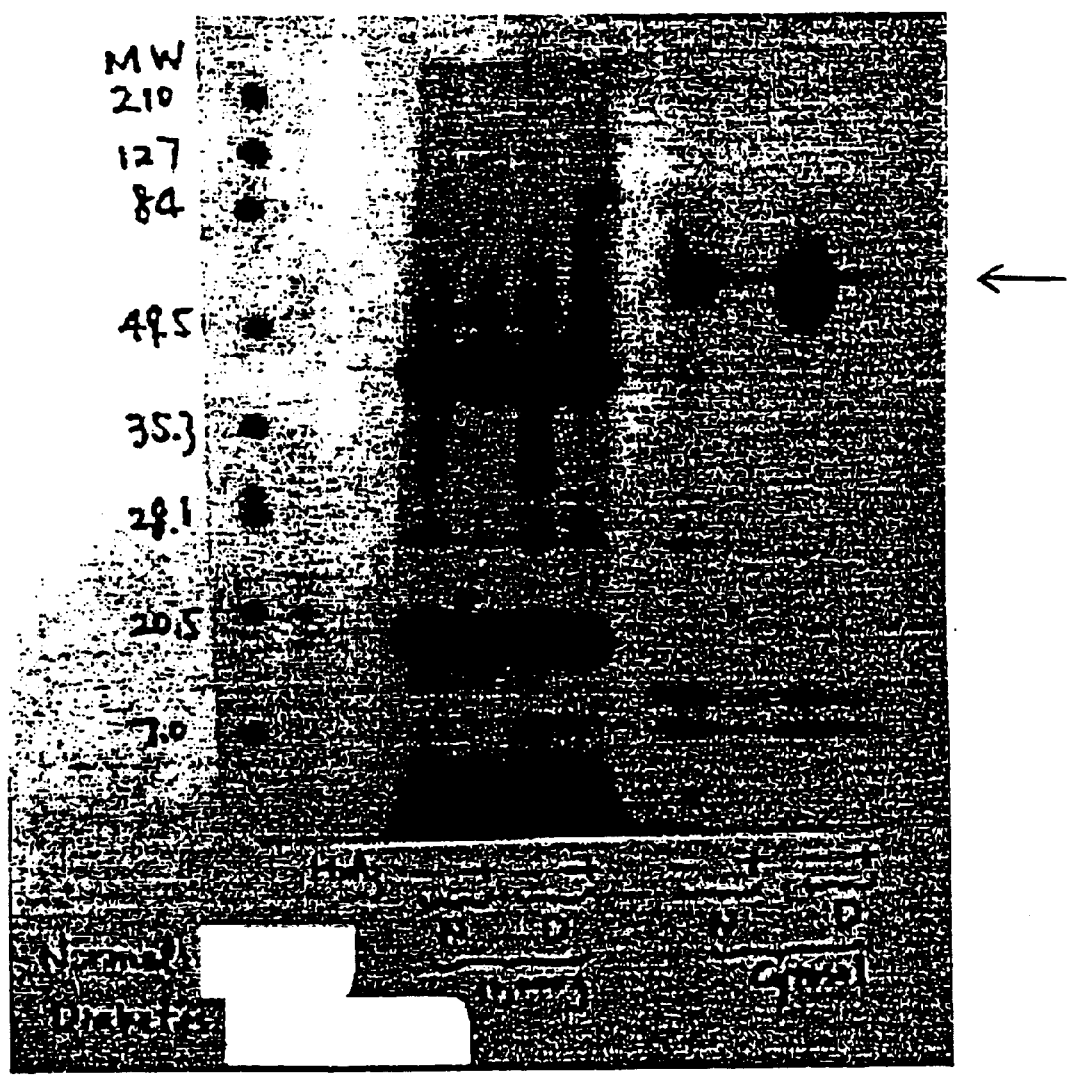
FIG. 7 shows 1D-PAGE analysis of the neutrophil HX binding protein from normal and Type 1 diabetic subjects after u.v. cross-linking with radioiodinated hepoxilin photoligand.

Previous studies demonstrated that hepoxilin binding takes place in human neutrophils. It is now demonstrated that the binding of tritiated native hepoxilin was altered in diabetic human subjects especially in Type 1 subjects (FIG. 6). It was then explored whether this binding was due to the presence of a protein through u.v. cross-linking with a photoaffinity radioiodinated ligand and subsequent SDS-PAGE analysis. FIG. 7 shows gel patterns comparing diabetic and normal hepoxilin binding in human neutrophils. A protein band around 60–70 kD is seen which is competitively antagonized by unlabeled hepoxilin showing specificity of binding. This band is diffuse in the Type 1 diabetic subject while that from the normal is quite distinct. This confirms earlier findings that the diabetic binding protein is possibly made up of isoforms or that the protein is modified. These studies have diagnostic potential in the pre-diabetic stage.

Figure 8:
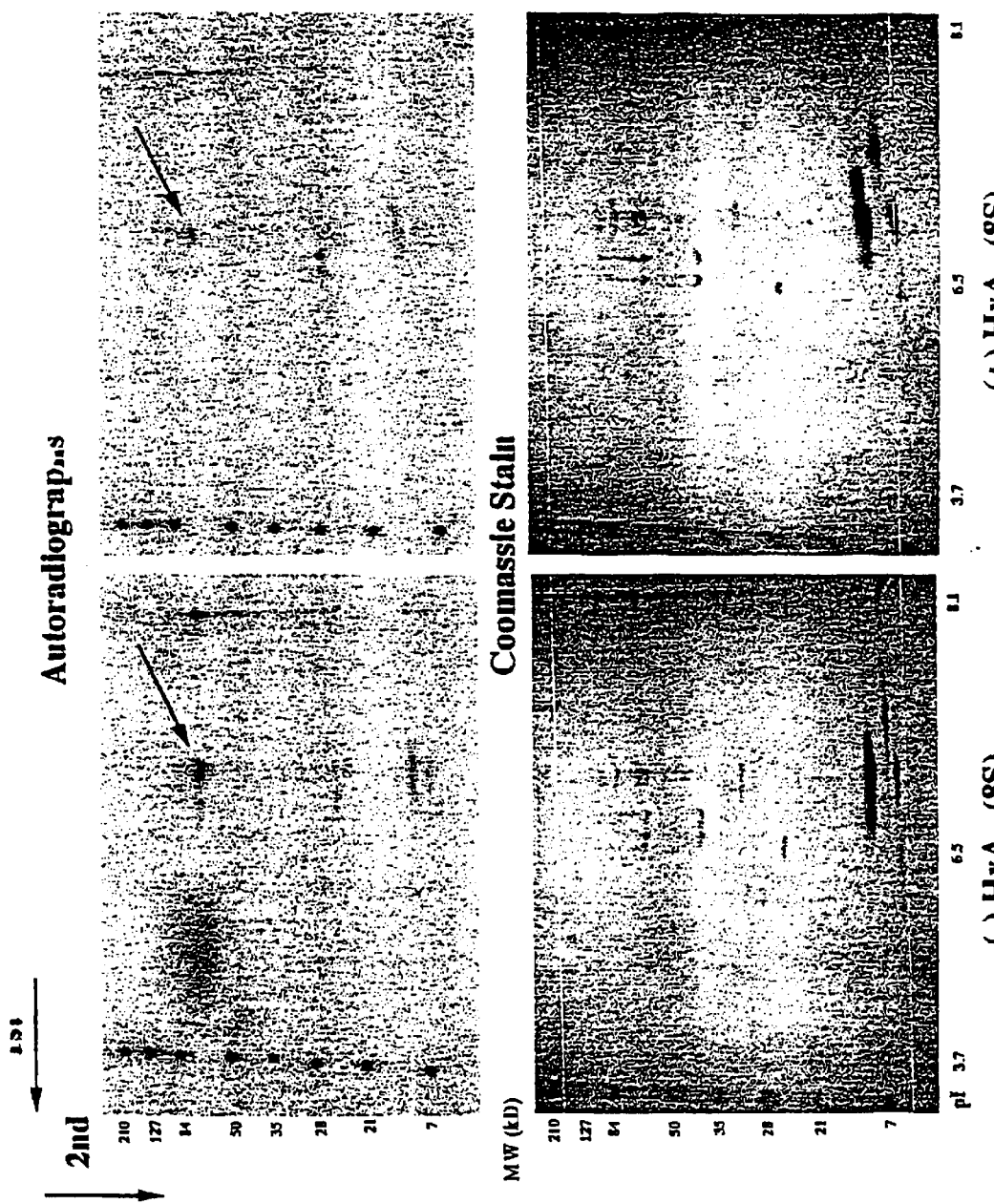
FIG. 8 shows 2D-PAGE analysis of the neutrophil binding protein from normal subjects showing the effect of addition of unlabeled HX. Note the single discreet radioactive 'spot'.

In FIG. 8 is shown a 2D PAGE for the normal protein; four panels show±$HxA_3$ for both Radioactivity (top panels) and Coomassie Blue (lower panels) staining. It is clear that the ~60 kD protein observed in the 1D PAGE is a distinct band with a pl around pH6. The resolution of the proteins is good enough to permit initial testing for 'purity' and to prepare tryptic digests to determine composition of the peptides as well as to investigate the localisation of the radioligand to specific peptides providing information on the binding sites.

Example 3

The Hepoxilin-binding Protein From Type 1 Diabetic Subjects is Resolved Into at Least Three Bands on 2D-PAGE'

We showed that the binding of tritiated HX to the diabetic neutrophil preparation was indeed significantly altered, especially in Type 1 subjects. We also showed that the SDS pattern of the Type 1 diabetic binding proteins was somewhat diffuse relative to the normal pattern (FIG. 7).

Figure 9:
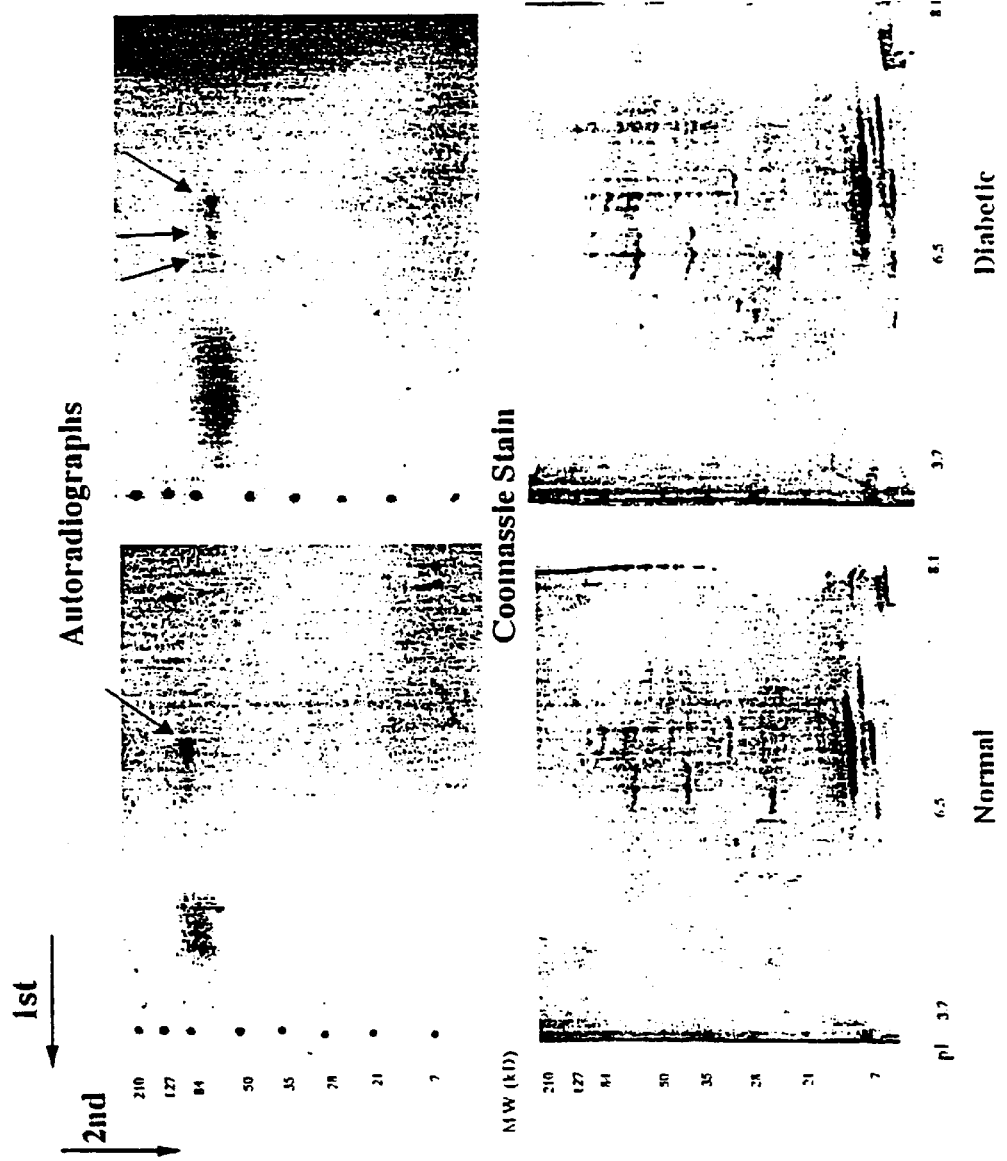
FIG. 9 shows 2D-PAGE analysis comparing the normal binding protein pattern with the protein pattern (isoforms) in Type 1 diabetic subjects.

Further analysis on 2D-PAGE demonstrated that the diffuse pattern in the Type 1 diabetics was resolved into three distinct proteins with similar MW but different pl (FIG. 9). Also note the intense broad pattern at the same MW but at a more acidic pl. This may result from extensive glycosylation of the diabetic binding proteins. This could provide a diagnostic means of 'typing' individuals predisposed to this disease, ie. the prediabetic stage.

Example 4

Human Neutrophils From Diabetic Subjects are More Responsive to a Dose Regimen of Native Hepoxilin Than Those From Normal Subjects in Terms of Calcium Release in Vitro.

It was previously reported that the native HX cause a rise in intracellular calcium in suspensions of human neutrophils. This rise is unaffected by extracellular medium devoid of calcium; hence HX causes a release of calcium from intracellular stores. Additionally it was shown that if HX is added a second time (5 min later) to the neutrophils, the second calcium response is inversely related to the rise elicited by the first challenge. suggesting depletion of calcium stores. Earlier studies also demonstrated that the calcium-release step was dependent on hepoxilin binding to its intracellular receptor. In view of the findings reported above on alterations in the hepoxilin binding protein in diabetes, it was investigated whether the response to varied amounts of hepoxilin in terms of calcium release was altered in Type 1 diabetic neutrophils. This involved measurement of the rise in intracellular calcium in INDO-1AM loaded neutrophil suspensions spectrofluorometrically after addition of $HxA_3$.

Figure 10:
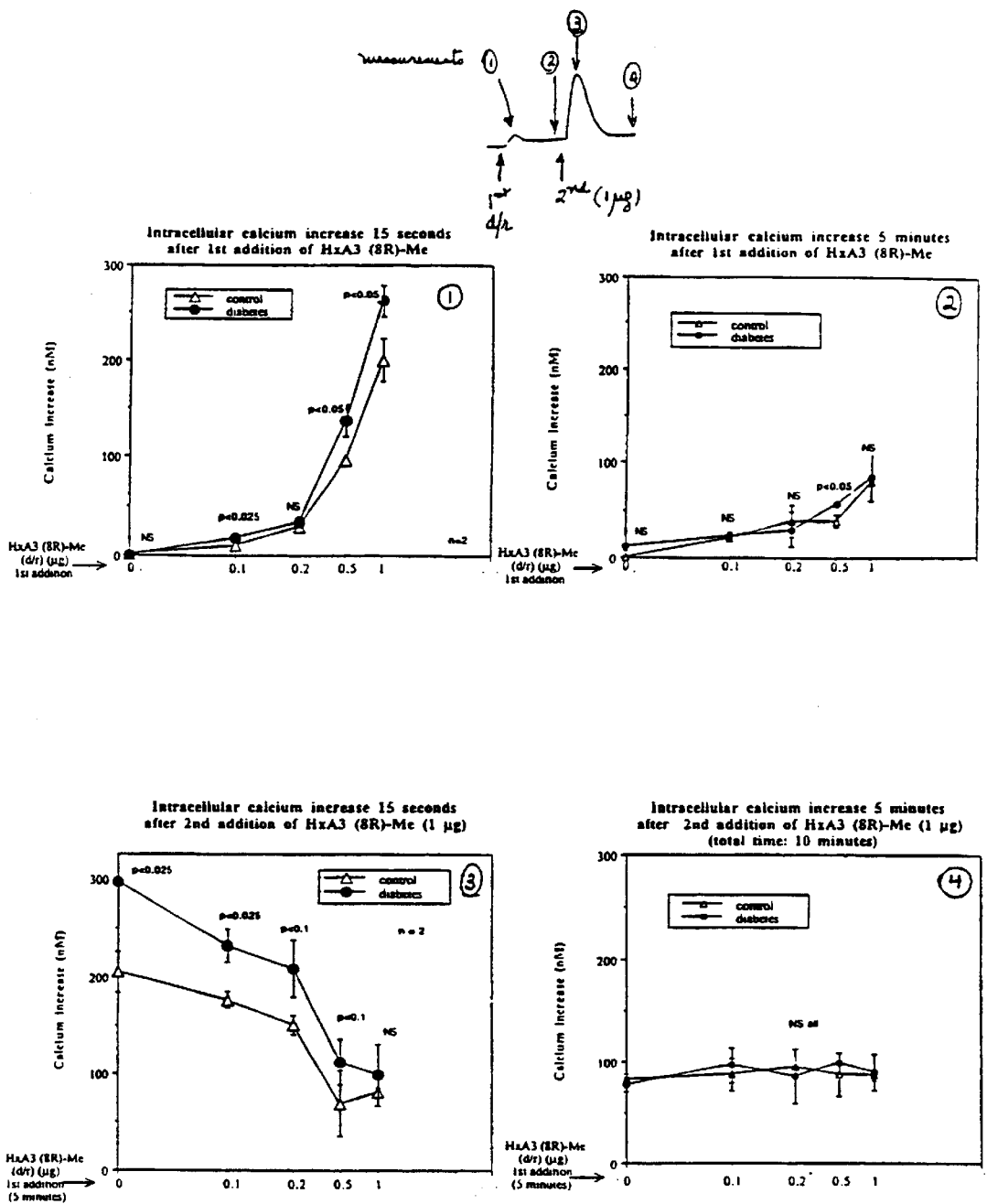
FIG. 10 shows a comparison between the normal and Type 1 diabetic neutrophils in their response to a rise in free calcium caused by different amounts of native HX.

Normal and diabetic neutrophils were compared to 4 concentrations of $HxA_3$, i.e. 100, 200, 500 and 1000 ng added in 1 $\mu$l DM50 to 2×$10^6$ cells/ml. Results (FIG. 10) showed that the diabetic neutrophils are more responsive to the hepoxilin than the normal cells. Additional data was obtained by administering 1000 ng of hepoxilin five minutes after the first test. Previous results with normal neutrophils have shown that the response to a second addition of hepoxilin is blunted depending on the extent of calcium rise in the first test. The diabetic neutrophils showed more inhibition but the end-response (i.e. at 5 min after hepoxilin challenge) was similar to normal neutrophils. These findings confirm a difference in binding/action of neutrophils from Type 1 diabetic subjects shown earlier with tritiated ligand.

Example 5
Inflammation

Figure 11:
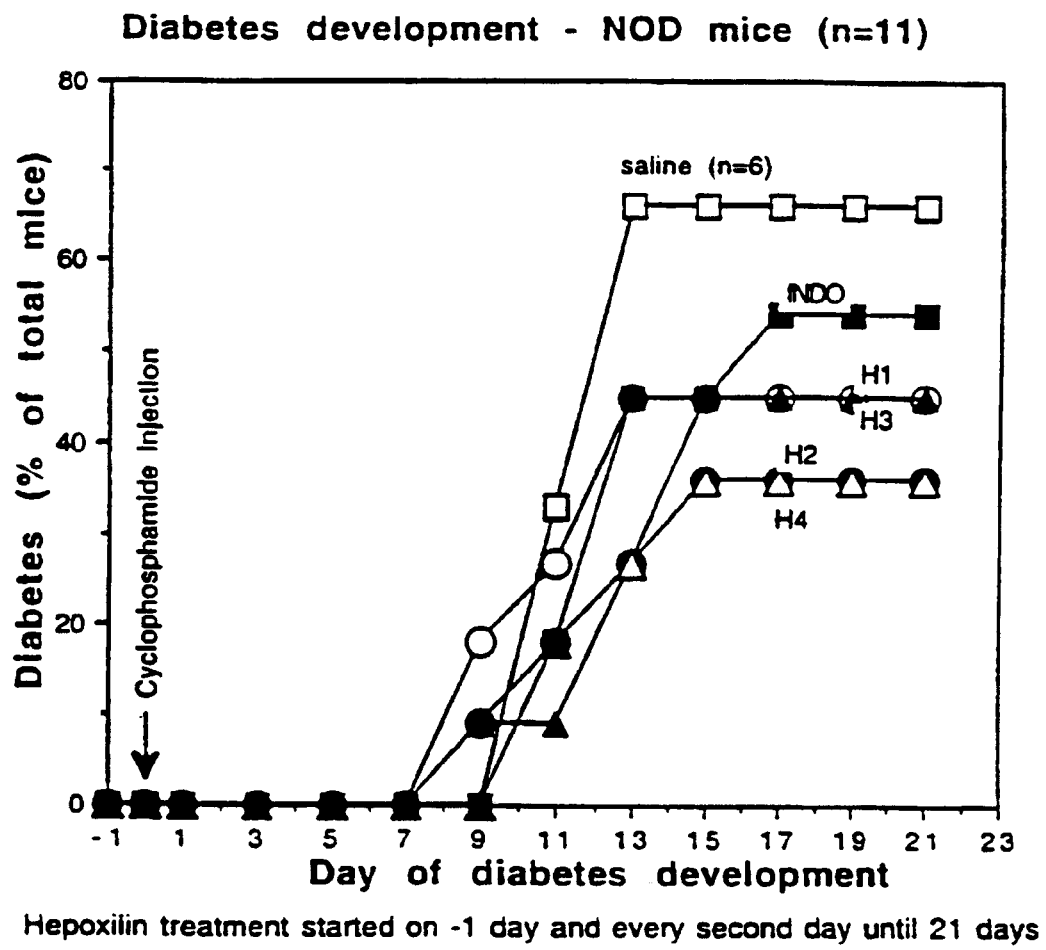
FIG. 11 shows diabetes onset (glucosuria) in NOD mice treated with cyclophosphamide i.p. and the effect of HX analogs (H1–H4) and Indomethacin administered before and every second day after cyclophosphamide injection. Each group was subdivided into subgroups of 5 and 6 mice and each subgroup was injected with test compounds on alternate days. All test compound-treated animals from both subgroups behaved in the same way, and the data are combined as shown.
Figure 12:
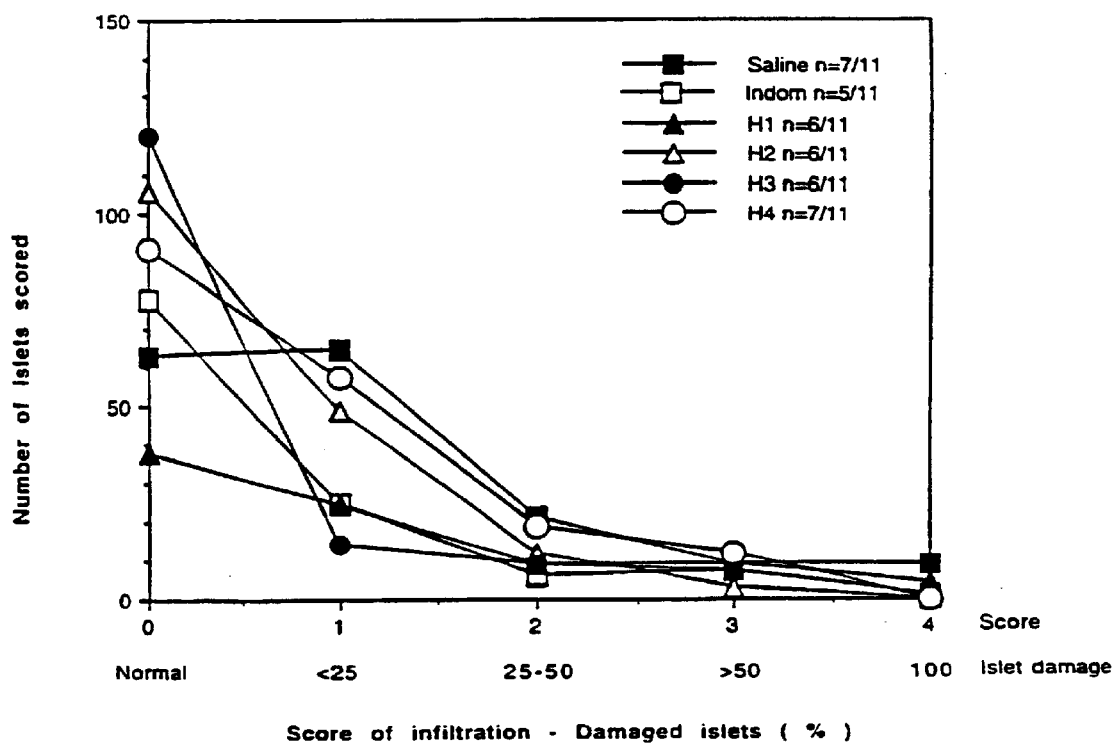
FIG. 12 shows the insulitis scores of the experiment in FIG. 11. The pancreas from the experiment in FIG. 11 was fixed and stained (H&E). Four sections were cut from each specimen and over 100 islets were observed for each group and scored for the degree of insulitis. Only islets from the non-diabetic animals were scored, as pancreata from diabetic animals would be devoid of islets. The graph shows the % insulitis for each group.

The Analogs Appear to Delay the Onset of Diabetes in the NOD Mouse Injected With Cyclophosphamide Mice (20 g body weight 6–8 wks old) were divided at random into 6 groups (11/group); all were administered cyclophosphamide (250 mg/kg) i.p. in a single time. Each group was further subdivided into 5 and 6 mice which were injected on separate days. Saline was given i.p. to group 1; indomethacin to group 2; the HX analogs to groups 3–6. HX analogs and the indomethacin were administered i.p one day before cyclophosphamide and subsequently every second day for 2 weeks at the dose of 50 µg/mouse (2500 µg/kg). After the first week, urine was tested for glucosuria with test strips. The animal was rendered diabetic if it tested positively for glucose in urine two days in a row. Diabetes onset is shown in FIG. 11. These results clearly show a difference in the rate of onset in the HX analog-treated groups relative to the saline-treated (cyclophosphamide-treated) groups. Histological examination of the pancreatic and splenic tissue in the animals confirmed that the severity of the disease (insulitis) was lessened in the HX analog-treated groups (attached 2 necropsy reports-pancreas and spleen). Cyclophosphamide administration causes splenic white pulp atrophy; this is observed in the saline-cyclophosphamide group while it appears to be 'milder' in the HX-analog-cyclophosphamide treated groups. We additionally scored the degree of damage (insulitis severity) in the islets remaining in the non-diabetic animals within each group to determine the extent of 'normalcy' in each group; 0 being normal, 1 being<25% insulitis, 2 being 25–50%, insulitis, 3 being>50% insulitis. FIG. 12 shows the results of these scores. While the islets in the saline group appear to be mostly at a score of 1, the HX analog-treated groups appear to have most of their islets at score 0, i.e normal. The results confirm the inhibitory effect of HX analog administration on glucosuria. The singular problem associated with the study was that one of the two saline subgroups (subgroup 1) unexpectedly did not develop diabetes (assessed by glucosuria) despite the histological data showing that the (nondiabetic) islets had an early form of insulitis, yet this was not severe enough to cause glucosuria, our marker for diabetes. The test compound-treated animals in this group developed diabetes to a similar extent as the subgroup 2. In the insulitis score, over 100 islets per group were scored. The results although preliminary with a relatively small number of animals (11) show potential in that the HX analogs appeared to weakly delay the onset of diabetes in the cyclophosphamide model. The effective concentration of the drugs may indeed be much less than that administered due to the still unknown extent of uptake and distribution in the body after i.p. administration.

Example 6
Hepoxilin Analogs Protect Against Lung Fibrosis in the Bleomycin-induced Lung Injury Model'

Mice were divided into 7 groups, each containing 5 animals. All groups were administered i.p. saline+7% ethanol as vehicle. Group 1 received only vehicle. Groups 2–7 received intratracheal bleomycin. Bleomycin is an antibiotic having antineoplastic activity. It is used clinically to treat malignancies such as lymphoma and testicular cancer. However, it has several side effects such as causing lung fibrosis characterized by diffuse alveolar hemorrhage and marked accumulation of inflammatory cells and an increase in collagen synthesis.

Additionally, Group 3 received Trolox antioxidant, Group 4 received H1, Group 5 received H2, Group 6 received H3, and Group 7 received H4.

Figure 13A:
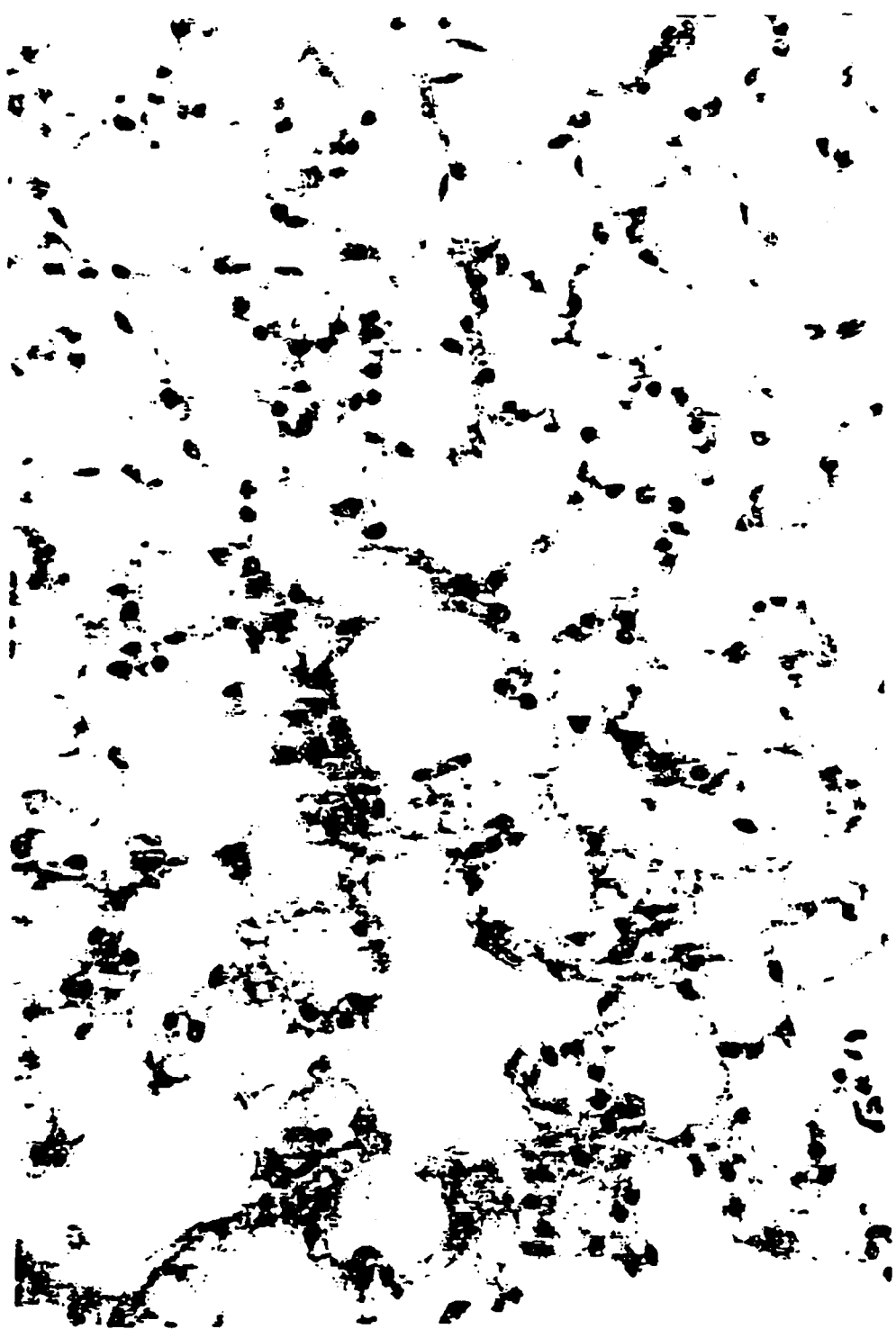
FIGS. 13A through 13G show the protective actions of HX analogs, especially H1, in a bleomycin-induced lung injury mouse model.
Figure 13B:
Figure 13C:
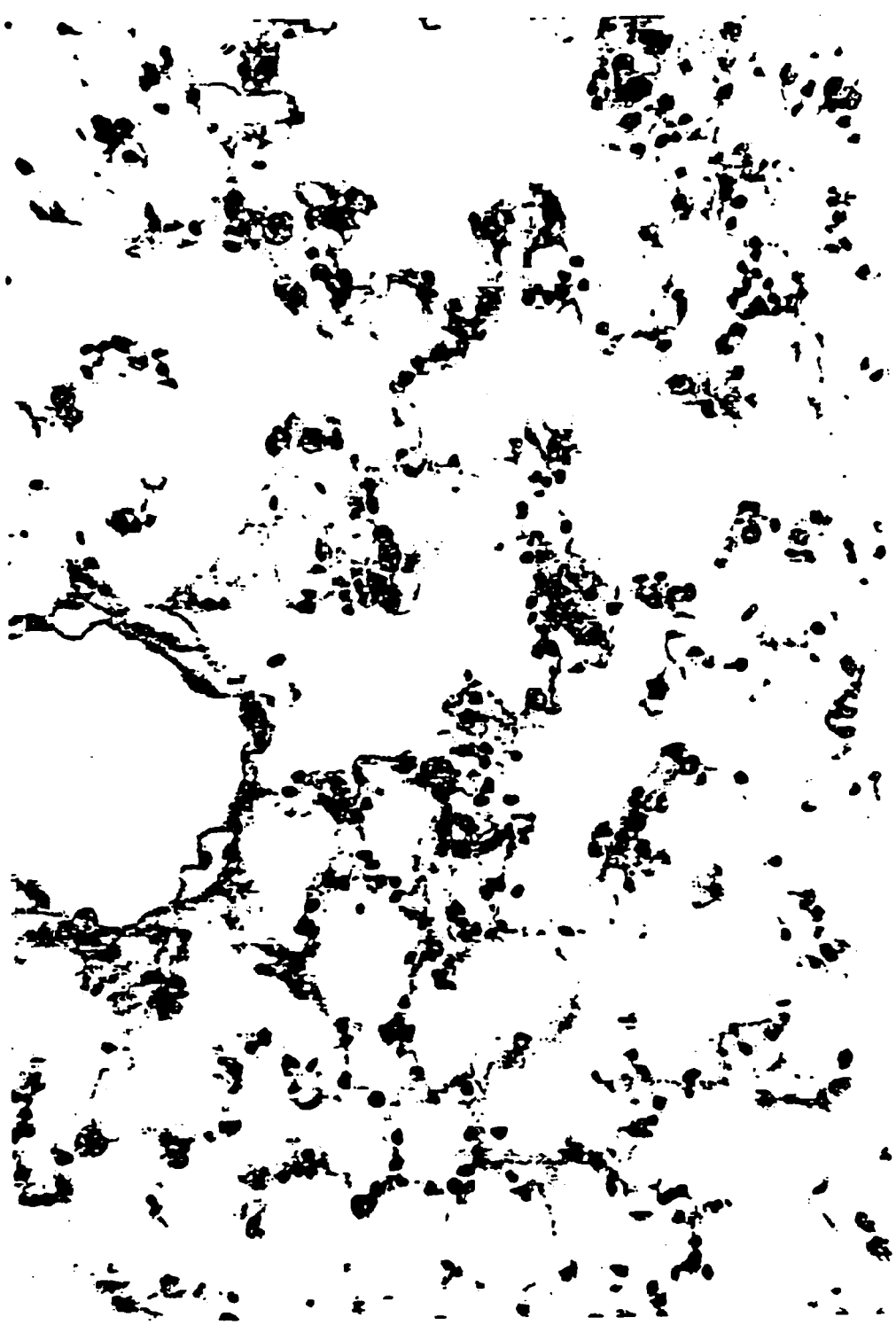
Figure 13:
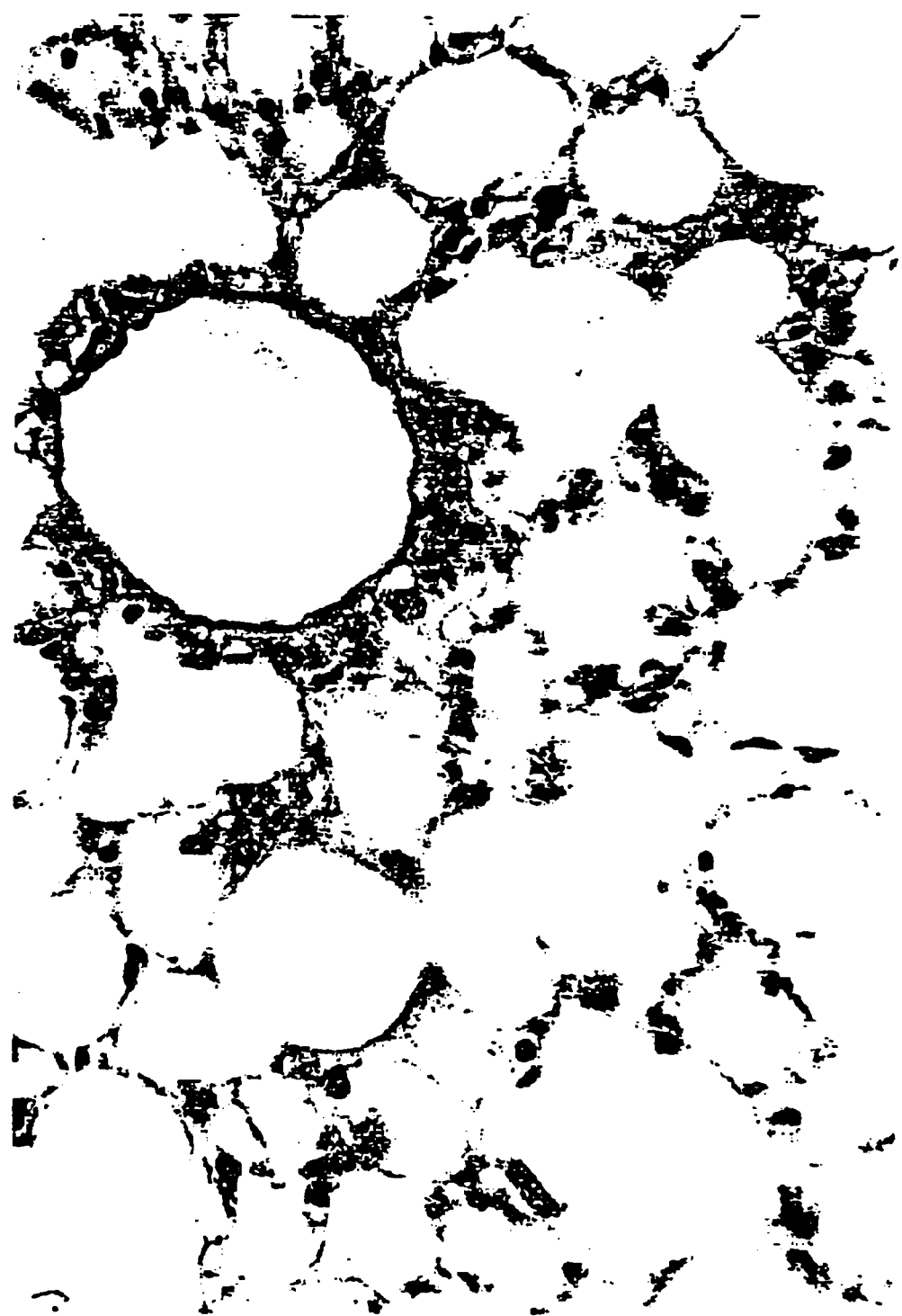
Figure 13E:
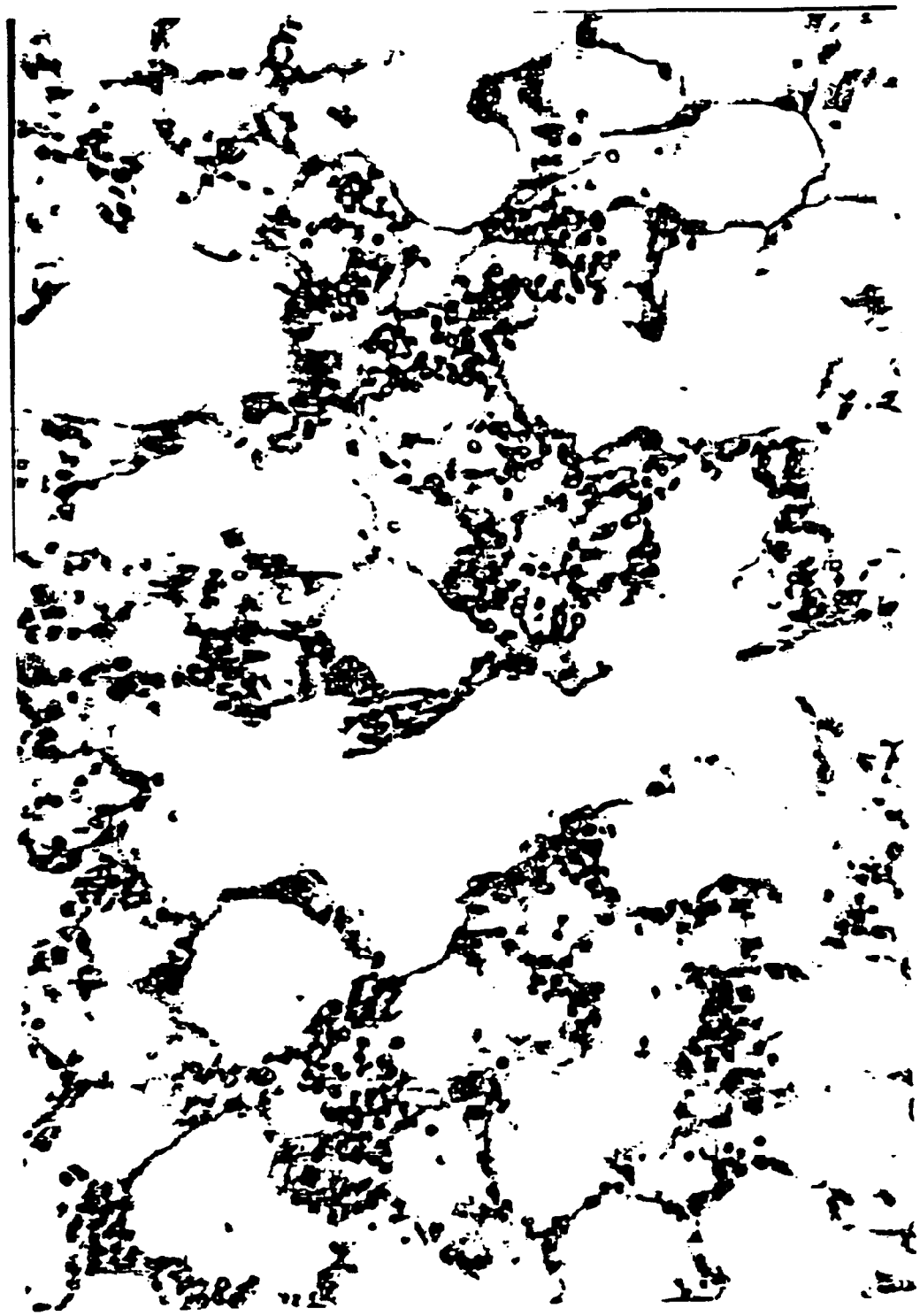
Figure 13F:
Figure 13G:

All hepoxilins were dissolved in 7 µl ethanol and diluted to 100 µl saline for i.p. administration. All compounds were administered daily at the dose of 100 µg/20 g (5000 µg/kg) mouse for 8 days. Lungs from all animals were perfused and fixed for histology. Analysis of histological sections of lungs by H&E staining indicated that the Bleomycin group showed strong evidence of fibrotic lesions with hemorrhage and the appearance of red blood cells (red streaks in the figure) and pulmonary fibrosis and some edema (FIG. 13B; compare the saline control FIG. 13A): the hepoxilin analog groups (H1–H4, FIGS. 13C–13F), although varied in potency, appear to inhibit these effects (see especially section for H1, FIG. 13C). As in section B1 above, the effective concentration of the drugs is unknown due to the still undetermined uptake and distribution in the body. The present study served as an indicator of biological activity in vivo.

The study was also conducted using saline or 200 µg/mouse bleomycin. In these studies the hepoxilin analogs H1 and H2 were administered in various concentrations (FIGS. 14A–14E). These studies indicated that hepoxilin analogs inhibited with different potencies the bleomycin-evoked lung fibrosis with H1 and 2 being most potent. H1 activity was dose dependent with a threshold activity at 400 µg/kg, i.p. H1 was more potent than Amifostine (200 mg/kg) or Trolox (30 mg/kg).

Figures 15A, 15B:
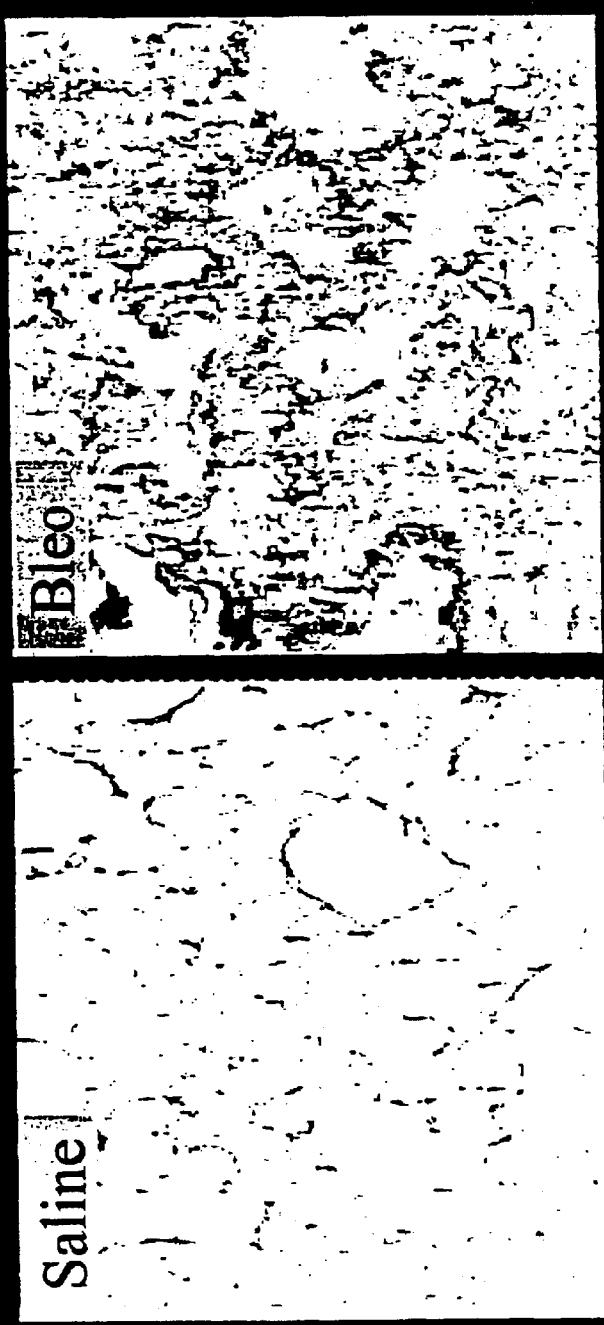
FIGS. 15A and 15B show collagen staining in a bleomycin-induced lung injury mouse model. Panel A is a saline control and Panel B is bleomycin.
Figures 16A, 16B, 16C, 16D, 16E:
FIGS. 16A through 16E show collagen staining in a bleomycin-induced lung injury mouse model at various concentrations of H1 (HXA-1). Panel A, saline control (no bleomycin); Panel B (bleomycin+saline), Panel C (bleomycin+400 µg/kg H1 in saline); Panel D (bleomycin+2 mg/kg H1 in saline); and, Panel E (bleomycin+4 mg/kg H1 in saline).
Figures 17A, 17B, 17C, 17D, 17E, 17F:
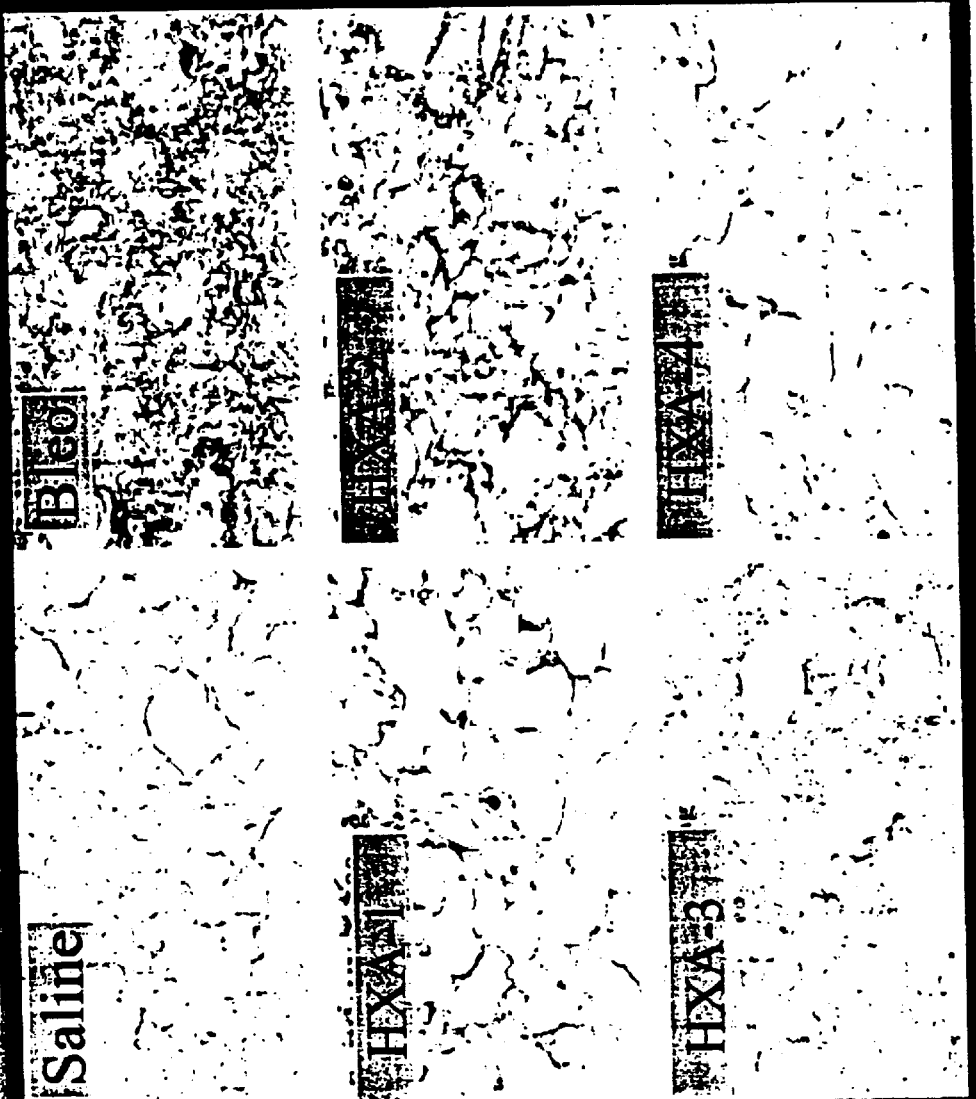
FIGS. 17A through 17F show the actions of HX analogs H1 to H4 (NXA-1 to HXA-4) on collagen synthesis by collagen staining in a bleomycin-induced lung injury mouse model. Panel 17A, saline control (no bleomycin); Panel 17B (bleomycin+saline); Panel 17C (bleomycin+H1 in saline); Panel 17D (bleomycin+H2 in saline); Panel 17E (bleomycin+H3 in saline); and Panel 17F (bleomycin+H4 in saline).

Lung fibrosis was associated with increased collagen synthesis (FIGS. 15A, 15B). Administration of H1 decreased collagen synthesis in the bleomycin-induced lung injury mouse model (FIGS. 16A–16E). Similarly, H1 to H4 also decreased collagen synthesis in the model (FIGS. 17A–17F). Collagen staining was done using sirius red and fast green.

Figure 18:
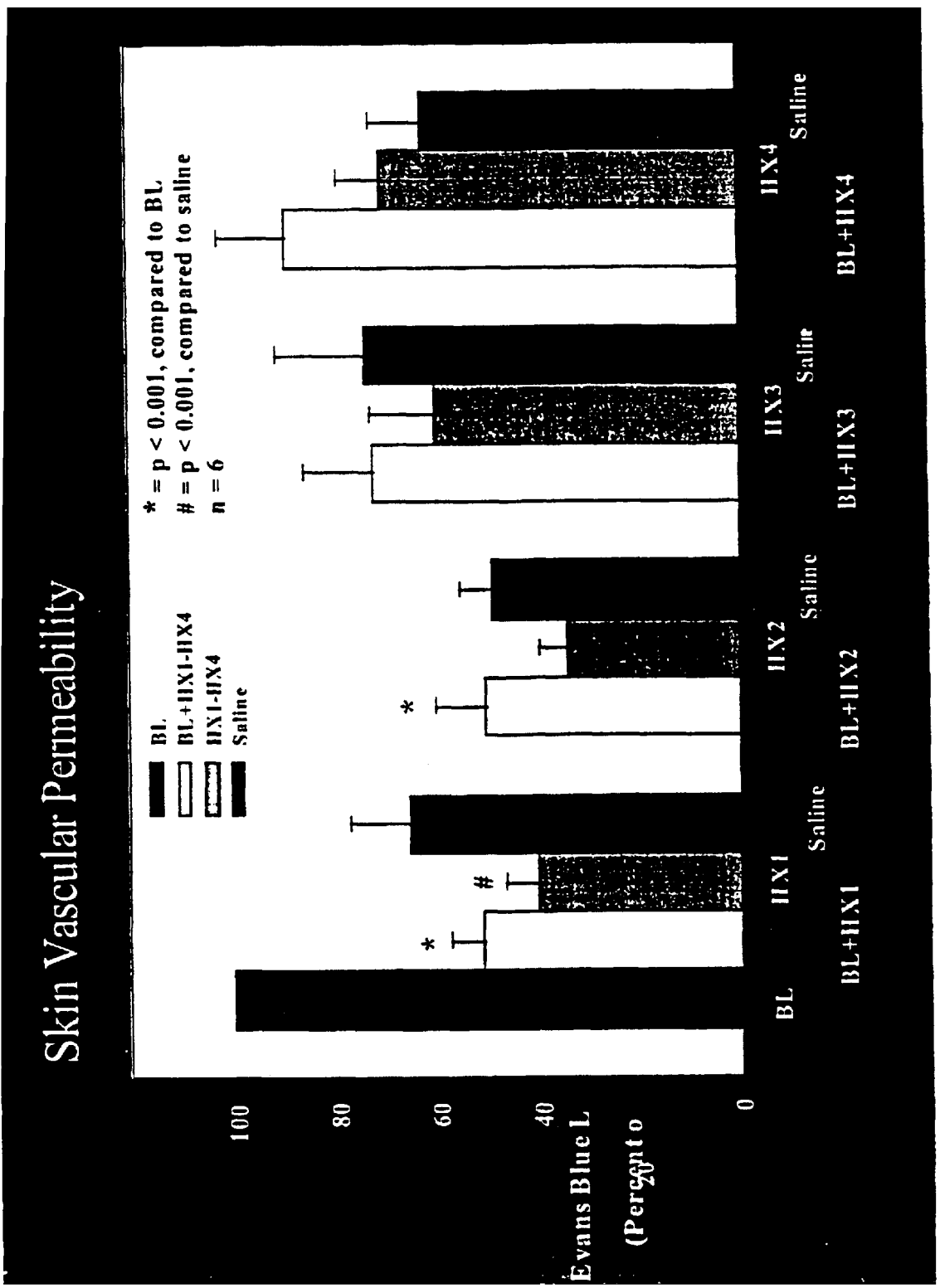
FIG. 18 shows the protective actions of HX analogs H1 to H4 (HX1 to HX4) on bleomycin-invoked skin vascular permeability.
Figure 17A:
Figure 19B:

H1 and 2 blocked the bleomycin (12 µg)—evoked vascular permeability at 100 ng intradermally. (FIGS. 18 and 19). Vascular permeability was measured using Evans Blue I.V. Hepoxilin analogs were intradermally applied and within 30 minutes, a formamide extraction of punched skin was done. Extraction and absorbance was read at 620 nm.

Example 7
Permeabilisation of Neutrophils—incorporation of GTP-γ-S

The method of Jaconi et al (1993, J. Biol. Chem. 268, 26077–26078] was employed with modifications to incorporate GTP-γ-S or GTP into human neutrophils. Specifically, $20 \times 10^6$ cells were incubated in 100 µl of sucrose-rich (500 mM) buffer containing in mM: NaCl 140, KCl 5, $MgCl_2$ 1, Hepes sodium-free 10, glucose 10, and EGTA 1, 10% polyetylene glycol 1000, pH 7.3. The buffer either contained nothing else (control) or GTP-γ-S (50 mM) or GTP (50 mM). The cells were incubated for 15 min at 37° C. to allow fluid-phase endocytosis of extracellular material. The cells were hypotonically shocked during 2 min at 37° C. by the addition of 1 mL of hypotonic medium made up of 1 part normal medium and 0.66 parts of water [Hallet & Campbell. 1983, Immunology, 50, 487–495]. The cells were then centrifuged at 900 rpm×5 min and resuspended in 2 mL of calcium-free assay medium for the binding studies or in RPMI 1640 for the calcium measurements. The extent of permeabilization was approximated in 4×10⁶ cells using Lucifer yellow [Jaconi et al 1993, J. Biol. Chem. 268, 26075–26078] at a concentration of 1 mg/mL in the permeabilizing medium. Both permeabilized and nonpermeabilized cells were investigated (as described above). The cells were finally washed four times with calcium-free medium and sonicated. The particulate matter was sedimented through centrifugation and fluorescence in the supernatant was measured in a fluorescence spectrophotometer and 430 nm excitation, 540 nm emission using dilutions of the dye as standard. While unshocked neutrophils contained virtually no fluorescence above background, the shocked cells contained approximately 24 ng dye/4×10⁶ cells. Assuming a cell volume of approximately 0.5 pL [Jaconi et al 1993, J. Biol. Chem. 268, 26075–26078], the equivalent concentration of cytosolic GTP-γ-S that is incorporated per cell from 50 mM is estimated at 21 $\mu$M.

Binding Studies

The binding assay was conducted in a clear medium (composition in mM: NaCl 140, KCl 5, MgCl$_2$ 1, CaCl$_2$1, HEPES sodium-free 10, and glucose 10, pH 7.3) containing the neutrophil suspension (2×10⁶ cells/tube) and [³H₆]-HxA$_3$ (8S) (50,000 cpm) in the presence or absence of 1 $\mu$g of unlabeled HxA$_3$ (8S) (in 2 $\mu$l DMSO) to determine the total and non-specific binding. All binding experiments were carried out in 1 mL at 37° C. for 60 min and performed in duplicates. The reaction was started by the addition of the cells in the medium containing the radioactive ligand (and the unlabeled ligand where specified). The binding reactions were terminated after the appropriate incubation times by isolation of the ligand-receptor complexes through vacuum filtration through Whatman GF/B glass fiber filters (Maidstone, England) prewashed with the clear medium. The tubes and the filters were washed with 3×3 mL of ice-cold medium. The radioactivity retained on the filters was counted in 10 mL of Ecolite scintillation fluid (ICN, St Laurent, Quebec) in a Beckman (Model LS 3800) liquid scintillation counter. Neutrophil membranes equivalent to 2×106 cells/tube were prepared by sonication (Model XL 2020, Sonicator Ultrasonic Processor, Heat Systems Inc., Farmingdale, N.Y.) of the cells and centrifugation.

Measurement of Intracellular Free Calcium

Intracellular free calcium concentrations were monitored continuously in a Perkin-Elmer fluorescence spectrophotometer (Model 65040) using Indo-I AM-loaded neutrophils. Excitation wavelength was set at 331 nm, emission wavelength at 410 nm., with slits of excitation and emission set at 3 and 15 nm respectively. Neutrophil suspensions (10⁷ cells) (normal or shocked cells) were loaded in RPMI 1640 medium with 3 $\mu$L of 1 mM (final concentration 3 $\mu$M) of the acetoxymethyl ester precursor of Indo-1 for 30 min at 37° C.

Unloaded dye was removed by centrifugation and the cells were resuspended in fresh RPMI 1640(1 mL). Dye-loaded cells were kept at room temperature on a rotator (RotoTorque, Cole-Palmer model 7637, USA) turning at about 10–15 rotations/min. Typical measurements involved 2×10⁶ cells in 1 mL of calcium-free assay medium (composition in mM: NaCl 140, KCl 5, MgCl$_2$ 1, Hcpcs sodium-free 10, glucose 10, and EGTA 1, pH 7.3) in a temperature controlled plastic cuvette (Diamed Labs., Canada) at 37° C. with constant stirring. Each measurement was followed by a calibration for maximum and minimum calcium release with ionomycin (1 $\mu$M final concentration) and MnCl$_2$ (3 mM final concentration) respectively according to Grinstein and Furuya [1984, BBRC, 122, 755–762].

Figure 20:
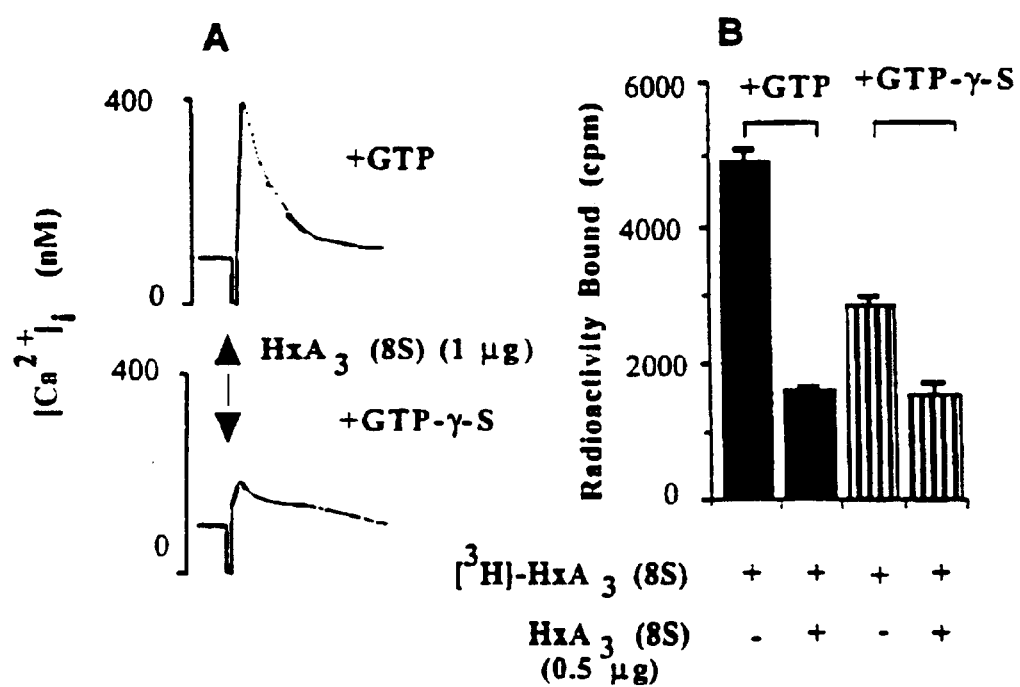
FIG. 20 shows the inhibition of the hepoxilin $A_3$-induced rise in intracellular calcium and binding of tritiated native hepoxilin $A_3$ ([$^3$H]-HxA$_3$(8S) in neutrophils into which cytosolic GTP-γ-S was incorporated through brief hypertonic/hypotonic shock (see Methods for details). Neutrophils ($2 \times 10^6$ cells/determination) were used in 1 mL calcium-free buffer at 37° C. with continuous stirring. Control experiments (not shown) with Lucifer yellow indicated that while no dye was incorporated in normal cells, the brief hypertonic/hypotonic shock procedure led to the internalization of dye equivalent to an approximate cytosolic concentration of GTP-γ-S (or GTP) of 21 µM. For measurement of intracellular calcium, the cells were centrifuged and loaded with INDO-1 AM (see Methods for details). The change in intracellular calcium was monitored with fluorescence spectrophotometer at 331 nm excitation and 410 nm emission. Note the rapid rise in intracellular calcium caused by $HxA_3$ and its inhibition only in the cells into which GTP-γ-S has been internalised (panel A). Cells into which GTP was internalised showed no significant change in the response to $HxA_3$ from control cells which were shocked in the absence of either nucleoside. A similar observation was made with binding of $[^3H]$-$HxA_3$ (panel B). Data represents the Mean±SD (n=4 separate experiments).

The resulting effect was recorded on a chart recorder (LKB model 2210, Pharmacia, Sweden) at 1 cm/min chart speed for the next 5 min (FIG. 20).

Measurement of cAMP and cGMP

Figure 21:
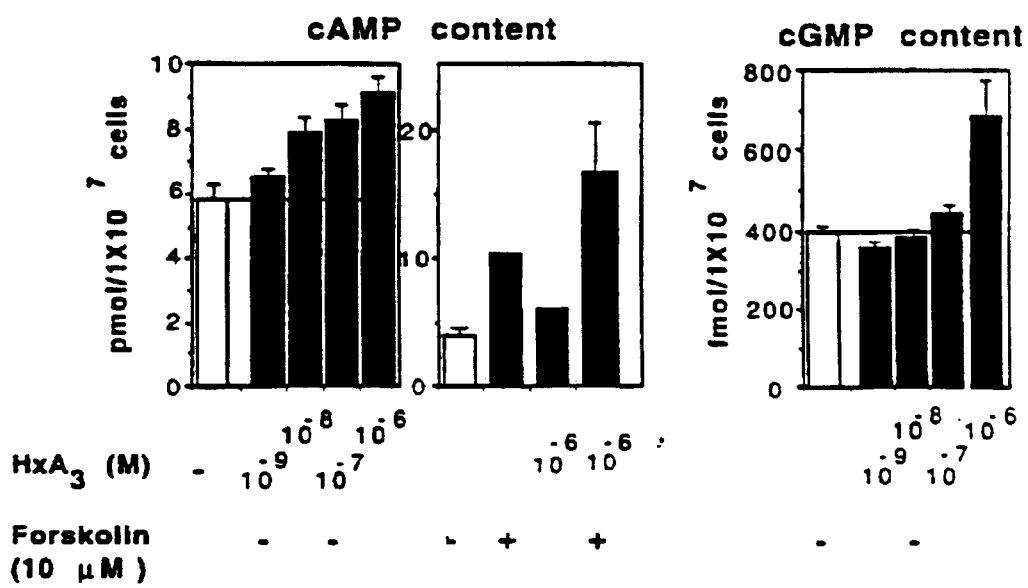
FIG. 21 shows the changes in the cellular content of cAMP (left panel) and cGMP (right panel) evoked by different concentrations of $HxA_3$ (8S). The effect of 10 μM Forskolin is shown (middle panel).

Human neutrophils (1×10⁷ cells) in 1 $\mu$L of assay buffer were preincubated with/without Forskolin (10 $\mu$M) during 10 min at 37°. DMSO (1 $\mu$L) alone (control) or containing various concentrations of HxA$_3$ (10⁻⁹ to 10⁻⁶ M final concentration) was added and the cells were incubated for a further 5 min. The reaction was stopped by the addition of 12% TCA and the samples were sonicated (4×3 sec). The samples were left on ice for 60 min to extract cAMP and cGMP. After centrifugation at 2500 g for 15 min, the supernatants were transferred and extracted with 5×5 mL water-saturated diethyl ether to remove the TCA. The aqueous phase was transferred and lyophilised. cAMP and cGMP were measured using specific double antibody RIA kits with ¹²⁵I-labeled cAMP or cGMP according to the instructions by the manufacturer (Amersham). Results are expressed in pmol/10 million cells for cAMP and in pmol/10 million cells for cGMP. Experiments were performed in triplicate for each point and repeated twice (FIG. 21).

Although preferred embodiments have been described herein in detail, it is apparent that changes may be made thereto without departing from the spirit of the present invention.

I claim:

1. A method for stimulating insulin secretion in a mammal comprising administering to the mammal an effective amount of a hepoxilin or of a compound of the formula

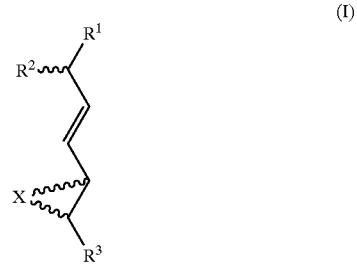

(I)

wherein X=O, CH$_2$, S or NH;

R$^1$=lower alkyl or alkene;
  lower alcohol (C1 to C22), saturated or unsaturated; or
  —CH$_2$CH=CH—(CH$_2$)$_3$—COR" wherein R"=OH or O—lower alkyl or alkene;

R$^2$=OH, NH$_2$, SH, OPO$_3$H, lower alkyl or alkene or O—lower alkyl or alkene; and R$^3$=lower alkyl or alkene or
  —CH$_2$—CH=CH—(CH$_2$)$_4$—R'" wherein R'"=CH$_3$, CH$_2$OH or CH$_2$
  —O—lower alkyl or alkene or

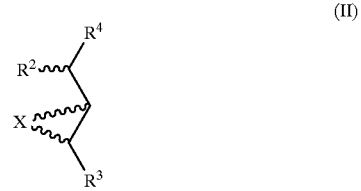

(II)

wherein X, $R^2$ and $R^3$ are as in formula I and $R^4$ =lower alkyl or alkene;
lower alcohol (C1 to C22), saturated or unsaturated; or
—CH=CH—CH$_2$—CH =CH—(CH$_2$)$_3$—COR"
wherein R"=OH or O—lower alkyl or alkene.

2. The method of claim 1 wherein the method comprises administering an effective amount of a compound selected from the group consisting of
   (a) 8(S)-hydroxy-11,12-cyclopropyl-eicosa-5Z, 10E, 14Z-trienoic acid or a lower alkyl or alkene ester derivative thereof;
   (b) 8(R)-hydroxy-11,12-cyclopropyl-eicosa-5Z, 10E, 14Z-trienoic acid or a lower alkyl or alkene ester derivative thereof;
   (c) 10(S)-hydroxy-11,12-cyclopropyl-eicosa-5Z,8Z, 14Z-trienoic acid or a lower alkyl or alkene ester derivative thereof; and
   (d) 10(R)-hydroxy-11,12-cyclopropyl-eicosa-5Z,8Z, 14Z-trienoic acid or a lower alkyl or alkene ester derivative thereof.

3. The method of claim 1 wherein the mammal suffers from Type I or Type II diabetes.

4. A method for inhibiting the development of diabetes in a mammal disposed to developing diabetes comprising administering to the mammal an effective amount of a compound of the formula

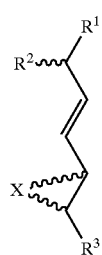

(I)

wherein X=O, CH$_2$, S or NH;
$R^1$=lower alkyl or alkene;
lower alcohol (C1 to C22), saturated or unsaturated; or
—CH$_2$CH=CH—(CH$_2$)$_3$—COR" wherein R"=OH or O—lower alkyl or alkene;
$R^2$=OH, NH$_2$, SH, OPO$_3$H, lower alkyl or alkene or O—lower alkyl or alkene; and
$R^3$=lower alkyl or alkene or
—CH$_2$—CH=CH—(CH$_2$)$_4$—R'" wherein R'"=CH$_3$, CH$_2$OH or CH$_2$
—O—lower alkyl or alkene or

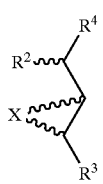

(II)

wherein X, $R^2$ and $R^3$ are as in formula I and $R^4$=lower alkyl or alkene;
lower alcohol (C1 to C22), saturated or unsaturated; or
—CH=CH—CH$_2$—CH=CH—(CH$_2$)$_3$—COR"
wherein R"=OH or O—lower alkyl or alkene.

5. The method of claim 1 wherein the mammal is a human.

6. The method of claim 2 wherein the mammal suffers from Type I or Type II diabetes.

7. The method of claim 4 wherein the mammal is a human.

8. The method of claim 4 wherein the method comprises administering an effective amount of a compound selected from the group consisting of
   (a) 8(S)-hydroxy-11,12-cyclopropyl-eicosa-5Z, 10E, 14Z-trienoic acid or a lower alkyl or alkene ester derivative thereof;
   (b) 8(R)-hydroxy-11,12-cyclopropyl-eicosa-5Z, 10E, 14Z-trienoic acid or a lower alkyl or alkene ester derivative thereof;
   (c) 10(S)-hydroxy-11,12-cyclopropyl-eicosa-5Z,8Z, 14Z-trienoic acid or a lower alkyl or alkene ester derivative thereof; and
   (d) 10(R)-hydroxy-11,12-cyclopropyl-eicosa-5Z,8Z, 14Z-trienoic acid or a lower alkyl or alkene ester derivative thereof.

9. The method of claim 2 wherein the mammal is a human.

10. The method of claim 8 wherein the mammal is a human.

11. The method of claim 2 wherein the method comprises administering an effective amount of a compound selected from the group consisting of
    (a) 8(S)-hydroxy-11,12-cyclopropyl-eicosa-5Z, 10E, 14Z-trienoic acid or trienoic acid methyl ester;
    (b) 8(R)-hydroxy-11,12-cyclopropyl-eicosa-5Z, 10E, 14Z-trienoic acid or trienoic acid methyl ester;
    (c) 10(S)-hydroxy-11,12-cyclopropyl-eicosa-5Z,8Z, 14Z-trienoic acid or trienoic acid methyl ester; and
    (d) 10(R)-hydroxy-11,12-cyclopropyl-eicosa-5Z,8Z, 14Z-trienoic acid or trienoic acid methyl ester.

12. The method of claim 11 wherein the mammal is a human.

13. The method of claim 8 wherein the method comprises administering an effective amount of a compound selected from the group consisting of
    (a) 8(S)-hydroxy-11,12-cyclopropyl-eicosa-5Z, 10E, 14Z-trienoic acid or trienoic acid methyl ester;
    (b) 8(R)-hydroxy-11,12-cyclopropyl-eicosa-5Z, 10E, 14Z-trienoic acid or trienoic acid methyl ester;
    (c) 10(S)-hydroxy-11,12-cyclopropyl-eicosa-5Z,8Z, 14Z-trienoic acid or trienoic acid methyl ester; and
    (d) 10(R)-hydroxy-11,12-cyclopropyl-eicosa-5Z,8Z, 14Z-trienoic acid or trienoic acid methyl ester.

14. The method of claim 13 wherein the mammal is a human.

* * * * *

UNITED STATES PATENT AND TRADEMARK OFFICE
CERTIFICATE OF CORRECTION

PATENT NO. : 6,673,785 B1
APPLICATION NO. : 10/048863
DATED : January 6, 2004
INVENTOR(S) : Cecil R. Pace-Asciak Page 1 of 1

It is certified that error appears in the above-identified patent and that said Letters Patent is hereby corrected as shown below:

Col. 6, line 22, "10E," should read --9E,--;

Col. 6, line 24, "10E," should read --9E,--;

Claim 2, Col. 15, line 8, "10E," should read --9E,--;

Claim 2, Col. 15, line 11, "10E," should read --9E,--;

Claim 8, Col. 16, line 14, "10E," should read --9E,--;

Claim 8, Col. 16, line 17, "10E," should read --9E,--;

Claim 11, Col. 16, line 35, "10E," should read --9E,--;

Claim 11, Col. 16, line 37, "10E," should read --9E,--;

Claim 13, Col. 16, line 50, "10E," should read --9E,--; and

Claim 13, Col. 16, line 52, "10E," should read --9E,--.

Signed and Sealed this

Eighth Day of December, 2009

David J. Kappos
*Director of the United States Patent and Trademark Office*